United States Patent
Bilenko et al.

(10) Patent No.: US 9,987,383 B2
(45) Date of Patent: Jun. 5, 2018

(54) MEDICAL DEVICE TREATMENT

(71) Applicant: Sensor Electronic Technology, Inc., Columbia, SC (US)

(72) Inventors: Yuri Bilenko, Columbia, SC (US); Timothy James Bettles, Columbia, SC (US); Alexander Dobrinsky, Loudonville, NY (US); Michael Shur, Latham, NY (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days. days.

(21) Appl. No.: 15/138,432

(22) Filed: Apr. 26, 2016

(65) Prior Publication Data
US 2016/0324996 A1   Nov. 10, 2016

Related U.S. Application Data

(60) Provisional application No. 62/158,023, filed on May 7, 2015.

(51) Int. Cl.
| | | |
|---|---|---|
| *A61L 2/10* | (2006.01) | |
| *A61B 7/02* | (2006.01) | |
| *A61L 2/24* | (2006.01) | |

(52) U.S. Cl.
CPC .................... *A61L 2/10* (2013.01); *A61B 7/02* (2013.01); *A61L 2/24* (2013.01); *A61L 2202/24* (2013.01)

(58) Field of Classification Search
USPC .................................................. 250/455.11
See application file for complete search history.

(56) References Cited

U.S. PATENT DOCUMENTS

| | | | |
|---|---|---|---|
| 5,892,233 A | 4/1999 | Clement | |
| 7,151,264 B2 * | 12/2006 | Ehlers, Sr. ........... | B01D 53/007 250/373 |
| 7,360,625 B2 | 4/2008 | Stickley | |
| 7,553,456 B2 | 6/2009 | Gaska et al. | |
| 7,634,996 B2 | 12/2009 | Gaska et al. | |
| 7,705,325 B2 | 4/2010 | Vestal | |
| 8,277,734 B2 | 10/2012 | Koudymov et al. | |
| 8,779,385 B2 * | 7/2014 | Noori ...................... | A61L 2/10 250/455.11 |
| 8,980,178 B2 | 3/2015 | Gaska et al. | |
| 9,006,680 B2 | 4/2015 | Bettles et al. | |
| 9,114,184 B2 * | 8/2015 | Messina ................ | A61L 2/10 |
| 9,138,499 B2 | 9/2015 | Bettles et al. | |
| 9,803,909 B2 * | 10/2017 | Son ....................... | F25D 17/04 |
| 2002/0074559 A1 * | 6/2002 | Dowling ................ | A61N 5/06 257/99 |
| 2011/0197921 A1 | 8/2011 | Rubin et al. | |
| 2012/0051969 A1 | 3/2012 | Nahman et al. | |

(Continued)

*Primary Examiner* — Phillip A Johnston
(74) *Attorney, Agent, or Firm* — LaBatt, LLC

(57) ABSTRACT

An ultraviolet illuminator for providing a cleaning treatment to a medical device is disclosed. The ultraviolet illuminator can include an ultraviolet cleaning treatment system that operates in conjunction with at least one ultraviolet radiation source and sensor to clean surfaces of a medical device for purposes of disinfection, sterilization, and/or sanitization. The ultraviolet illuminator is suitable for a wide variety of medical devices, instruments and equipment. Stethoscopes and medical instrument probes are illustrative examples of some devices that can be used with the ultraviolet illuminator.

20 Claims, 9 Drawing Sheets

(56) References Cited

U.S. PATENT DOCUMENTS

| | | |
|---|---|---|
| 2013/0048545 A1 | 2/2013 | Shatalov et al. |
| 2013/0270445 A1 | 10/2013 | Gaska et al. |
| 2014/0001374 A1 | 1/2014 | Ullman |
| 2014/0060094 A1 | 3/2014 | Shur et al. |
| 2014/0060095 A1 | 3/2014 | Shur et al. |
| 2014/0060096 A1 | 3/2014 | Shur et al. |
| 2014/0060104 A1 | 3/2014 | Shur et al. |
| 2014/0061509 A1 | 3/2014 | Shur et al. |
| 2014/0202962 A1 | 7/2014 | Bilenko et al. |
| 2014/0217307 A1 | 8/2014 | Messina et al. |
| 2015/0008167 A1 | 1/2015 | Shturm et al. |
| 2015/0069270 A1 | 3/2015 | Shur et al. |
| 2015/0165079 A1 | 6/2015 | Shur et al. |
| 2015/0217011 A1 | 8/2015 | Bettles et al. |
| 2015/0297767 A1 | 10/2015 | Gaska et al. |
| 2015/0336810 A1 | 11/2015 | Smetona et al. |
| 2016/0000953 A1 | 1/2016 | Bettles et al. |
| 2016/0058020 A1 | 3/2016 | Shur et al. |
| 2016/0074547 A1 | 3/2016 | Dobrinsky et al. |
| 2016/0106873 A1 | 4/2016 | Dobrinsky et al. |
| 2016/0114067 A1 | 4/2016 | Dobrinsky et al. |
| 2016/0114186 A1 | 4/2016 | Dobrinsky et al. |
| 2016/0128526 A1 | 5/2016 | Dobrinsky et al. |

\* cited by examiner

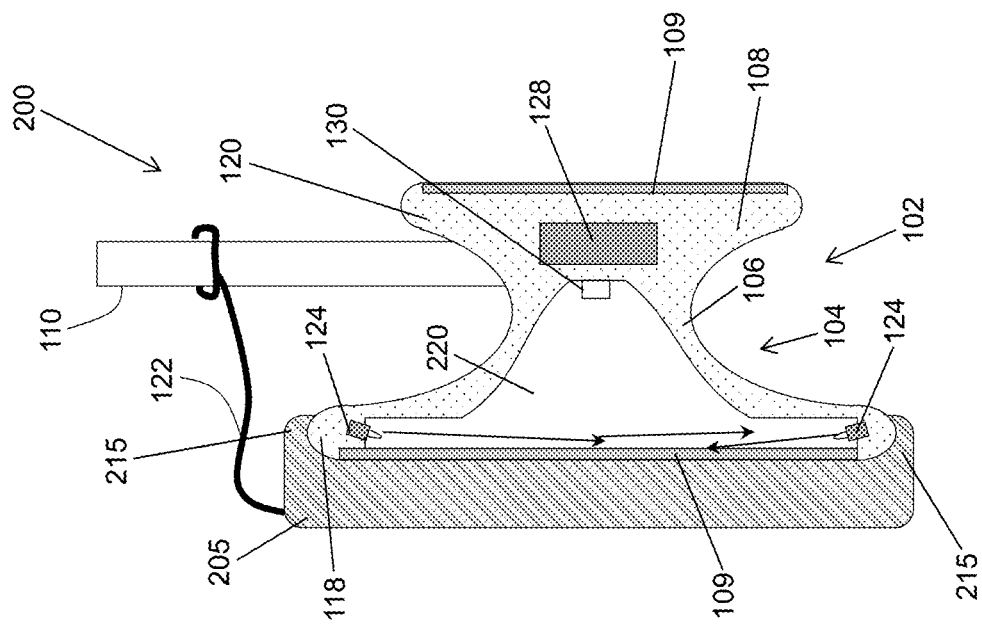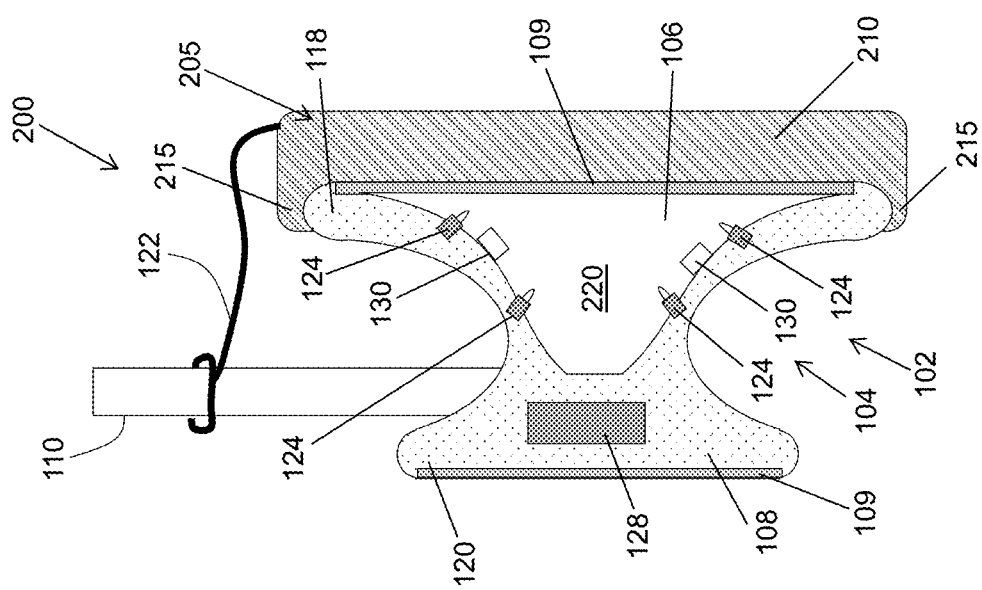

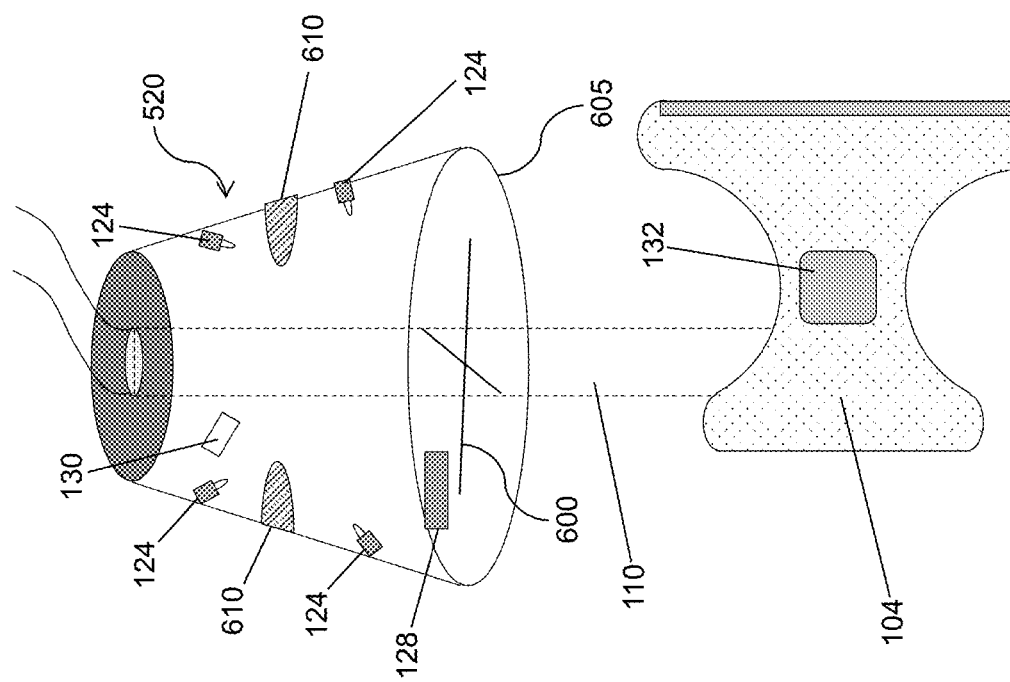
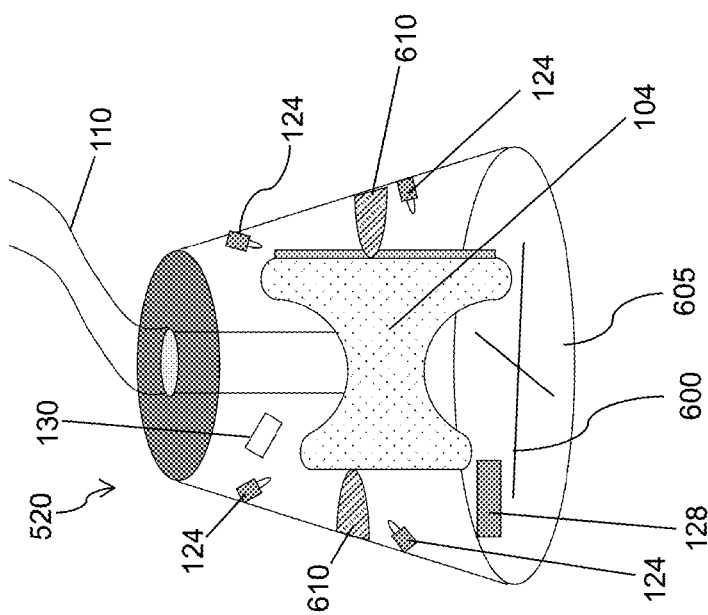
FIG. 6A
FIG. 6B

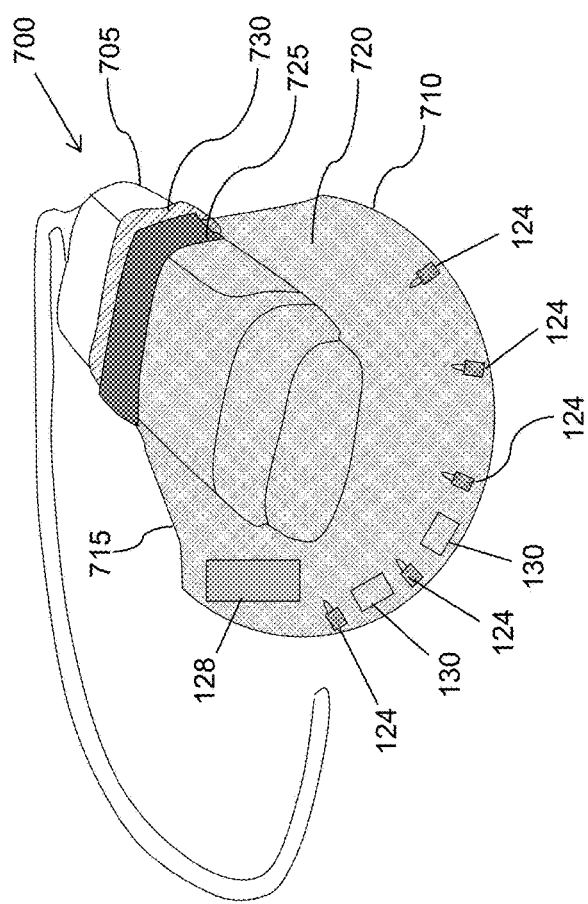
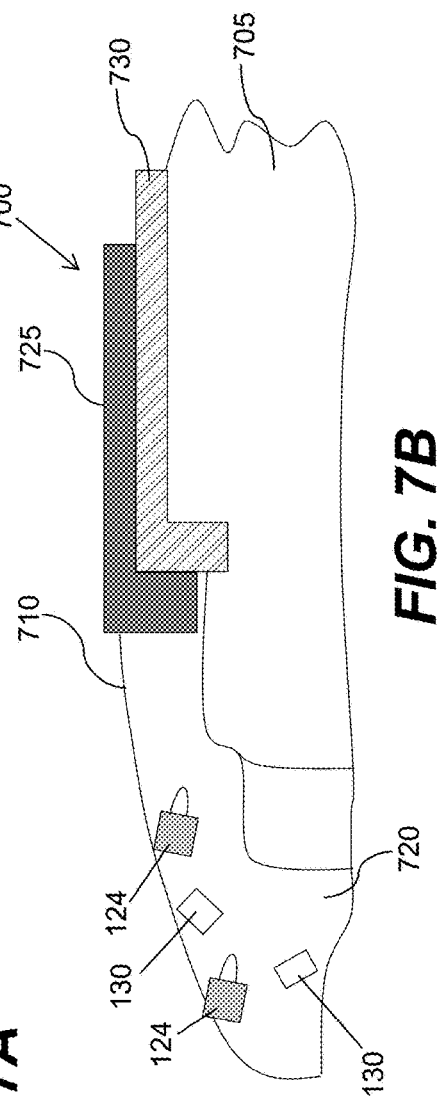

MEDICAL DEVICE TREATMENT

REFERENCE TO RELATED APPLICATIONS

The present patent application claims the benefit of U.S. Provisional Application No. 62/158,023, which was filed on 7 May 2015, and which is hereby incorporated by reference.

TECHNICAL FIELD

The disclosure relates generally to cleaning medical equipment, and more specifically, to a solution for using ultraviolet radiation for treating (e.g., disinfecting, sterilizing, sanitizing, and/or the like) a medical device.

BACKGROUND ART

A stethoscope is one example of a medical device in which ultraviolent radiation has been used for sterilization purposes. In one example, a box-shaped unit constructed of glass and plastic is used as a small sterilizer for a stethoscope. The box-shaped unit fits into a shirt or jacket pocket through a clip formed on the back of the unit. A U-shaped lip on the front of the unit leads into an opening that receives the chest piece of the stethoscope. Beneath the lip is a switch that operates on contact with the chest piece of the stethoscope to activate the unit. The unit is then powered by small pen light batteries. An ultraviolet light located proximate the U-shaped lip delivers ultraviolet light rays through a circular transparent window aligned with the chest piece of the stethoscope. In this manner, the unit can be used to simultaneously store and sterilize the chest piece of the stethoscope while within the pocket of a user during periods of non-usage.

In another example, a cover with an ultraviolet light source is used to sterilize the chest piece of the stethoscope. In particular, the cover is adapted to operably engage the chest piece such that the cover is movable with respect to a face portion of the chest piece that is used to contact a patient to listen to various pitched levels of sound emanating from the patient. In addition, the cover is normally biased to cover the face portion of the chest piece. The ultraviolet light source is positioned to illuminate the cover and the face portion of the chest piece only when the cover is covering the face portion. In this manner, the ultraviolet light source can provide anti-microbial sterilization of at least the face portion of the chest piece.

SUMMARY OF THE INVENTION

This Summary Of The Invention introduces a selection of certain concepts in a brief form that are further described below in the Detailed Description Of The Invention. It is not intended to exclusively identify key features or essential features of the claimed subject matter set forth in the Claims, nor is it intended as an aid in determining the scope of the claimed subject matter.

Aspects of the present invention are directed to an ultraviolet medical device illuminator having an ultraviolet cleaning treatment system for providing a cleaning treatment to a medical device such as, for example, a stethoscope, and other medical instruments and equipment containing similarly size elements that may need a cleaning treatment to remove bacteria, viruses, germs, and the like. The ultraviolet medical device illuminator and the accompanying ultraviolet cleaning treatment system for a medical device, such as a stethoscope, can include an ultraviolet light emitting diode (UV LED) based system that provides a cleaning treatment to one or more surfaces of the diaphragm and/or the bell that generally form a chest piece of the stethoscope. In particular, the UV LED based system can employ at least one UV LED source operating at a wavelength that ranges from about 260 nanometers (nm) to about 310 nm.

The UV LED source can be positioned in a housing having an opening into a reflecting cavity with a reflection coefficient of at least 50%, in which the stethoscope is held and irradiated by the UV LED source during a cleaning treatment. A control unit can determine whether the stethoscope needs a cleaning treatment upon being secured to the housing. The control unit can activate operation of the UV LED source if a cleaning treatment is necessary. The activating can include specifying a plurality of operating parameters for the cleaning treatment of the stethoscope. The plurality of operating parameters can include a cleaning treatment time that the UV LED source emits the ultraviolet radiation towards a surface of the stethoscope, a dosage of ultraviolet radiation delivered by the UV LED source, a power setting for operating the UV LED source, and a maximum operating temperature. A timer can be set in accordance with the specified cleaning treatment time in order to ensure that the UV LED source delivers a sufficient dosage for the corresponding cleaning treatment being performed on the stethoscope, e.g., disinfection, sterilization, sanitization, and/or the like. An input component can permit a user to adjust at least one of the plurality of operating parameters and an output component can indicate status information of the cleaning treatment (e.g., on, off, cleaned, needs cleaning, etc.). A power supply can provide power to all of the components of the UV LED based system to facilitate the cleaning treatment of the stethoscope.

A first aspect of the invention provides a system, comprising: an open-ended housing having a cavity formed therein that is configured to receive a medical device; at least one ultraviolet radiation source located within the cavity of the housing that is configured to emit ultraviolet radiation towards a surface of the medical device located within the cavity; a control unit that determines whether the medical device needs a cleaning treatment in response to the medical device being placed within the housing, the control unit activating operation of the ultraviolet radiation source in response to determining that the medical device needs a cleaning treatment, wherein the activating includes specifying a plurality of operating parameters for the cleaning treatment of the medical device, the plurality of operating parameters including a cleaning treatment time that the ultraviolet radiation source emits the ultraviolet radiation towards the surface of the medical device, a dosage of ultraviolet radiation delivered by the ultraviolet radiation source, a power setting for operating the ultraviolet radiation source, and a maximum operating temperature; an input component that permits a user to adjust at least one of the plurality of operating parameters; and an output component that provides status information of the cleaning treatment for use by the user.

A second aspect of the invention provides a stethoscope, comprising: a chest piece having a diaphragm and a bell; a binaural assembly having ear tips and ear tubes coupled to the ear tips; a tubing connecting the chest piece to the binaural assembly; and an ultraviolet cleaning system that is configured to administer a cleaning treatment to the chest piece and the binaural assembly, the ultraviolet cleaning system including: a set of housings, each housing with an opening to receive at least one of: the chest piece or an ear tip of the binaural assembly; at least one ultraviolet radiation source to emit ultraviolet radiation towards a surface of the chest piece and the binaural assembly; a control unit that determines whether at least one of: the chest piece or the binaural assembly, needs a cleaning treatment in response to one being secured to the housing, the control unit activating operation of the ultraviolet radiation source in response to determining that the at least one of the chest piece or the binaural assembly needs a cleaning treatment, the activating includes specifying a plurality of operating parameters for the cleaning treatment, the plurality of operating parameters including a cleaning treatment time that the ultraviolet radiation source emits the ultraviolet radiation towards the surface of the at least one of the chest piece or the binaural assembly, a dosage of ultraviolet radiation delivered by the ultraviolet radiation source, a power setting for operating the ultraviolet radiation source, and a maximum operating temperature; an input component that permits a user to adjust at least one of the plurality of operating parameters; and an output component that provides status information of the cleaning treatment for presentation to the user.

A third aspect of the invention provides a medical device cleaning container, comprising: a flexible receptacle having an opening to an inner surface that receives a medical device, wherein the inner surface is reflective to at least 30% and has a reflection coefficient of at least 50%, and an overlapping opening cover that covers the opening in response to the medical instrument being inserted therein and prevents ultraviolet radiation from escaping the receptacle during a cleaning treatment of the medical device; an ultraviolet cleaning system that is configured to administer a cleaning treatment to the medical device, the ultraviolet cleaning system including: at least one ultraviolet radiation source located within the receptacle that is configured to emit ultraviolet radiation towards a surface of the medical device; a control unit that determines whether the medical device needs a cleaning treatment in response to the medical device being inserted within the receptacle, the control unit activating operation of the ultraviolet radiation source in response to determining that the medical device needs a cleaning treatment, the activating includes specifying a plurality of operating parameters for the cleaning treatment of the medical device, the plurality of operating parameters including a cleaning treatment time that the ultraviolet radiation source emits the ultraviolet radiation towards the surface of the medical device, a dosage of ultraviolet radiation delivered by the ultraviolet radiation source, a power setting for operating the ultraviolet radiation source, and a maximum operating temperature; an input component that permits a user to adjust at least one of the plurality of operating parameters; and an output component that provides status information of the cleaning treatment for presentation to the user.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 2A-2B show schematics of cross-sectional views of an ultraviolet medical device illuminator in which ultraviolet radiation sources are integrated with a medical device according to an embodiment.

FIGS. 6A-6B show schematics of more detailed views of a slidable unit depicted in FIG. 5 according to an embodiment.

FIGS. 7A-7B show schematics of an ultraviolet medical device illuminator suitable for use with a medical probe instrument according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
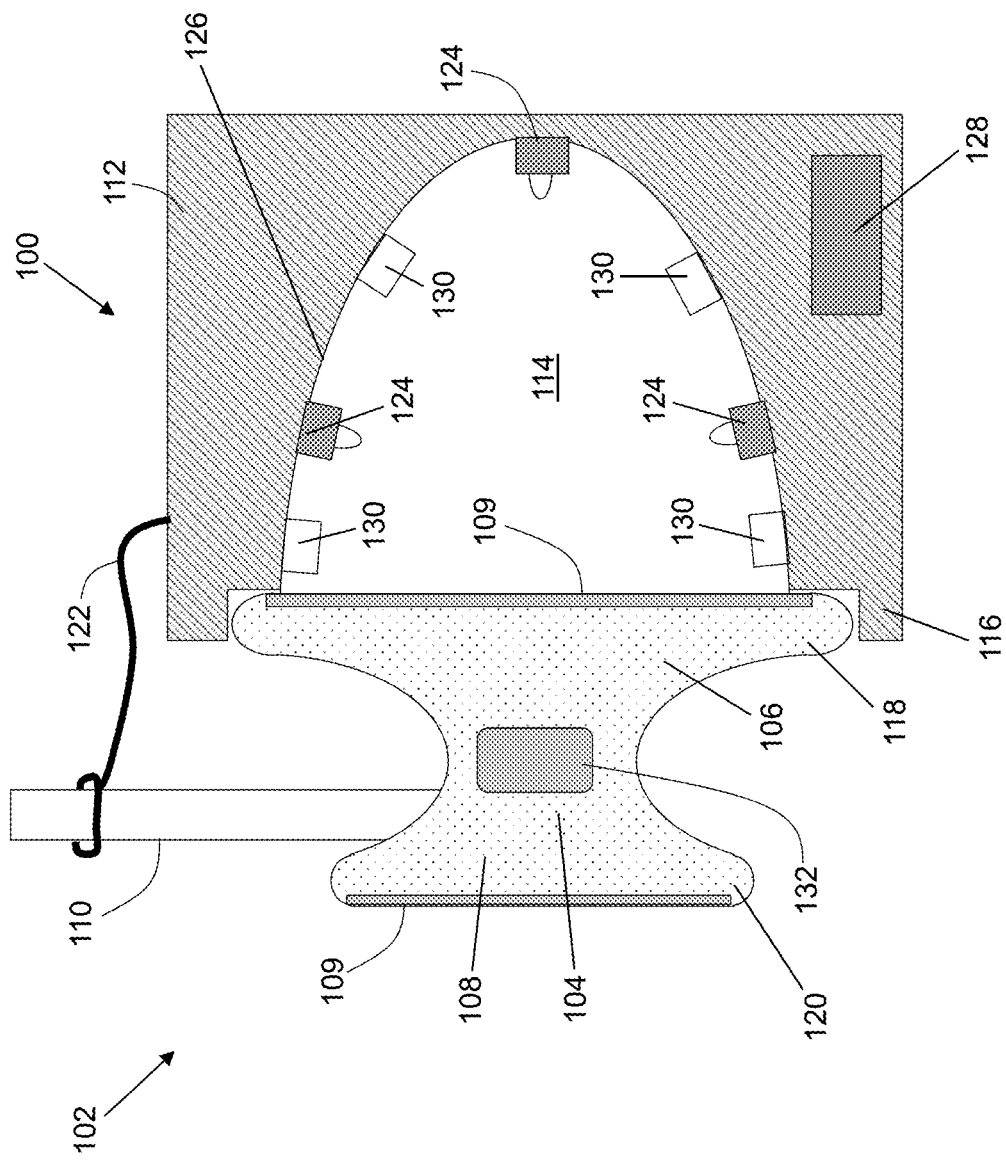
FIG. 1 shows a schematic of a cross-sectional view of an ultraviolet medical device illuminator coupled to a medical device according to an embodiment.

As indicated above, aspects of the invention are directed to an ultraviolet medical device illuminator for providing a cleaning treatment of a medical device such as, for example, a stethoscope, and other medical instruments and equipment containing similarly size elements that may need a cleaning treatment. The ultraviolet medical device illuminator can include an ultraviolet cleaning treatment system that facilitates a cleaning treatment of the medical device using ultraviolet radiation. The modalities used with the ultraviolet illuminator and the accompanying ultraviolet cleaning treatment system can include any now known or later developed approaches that incorporate the concepts of the various embodiments described herein.

As used herein, a cleaning treatment of a medical device can entail sanitizing, disinfecting, and/or sterilizing a medical device. Sanitizing generally means reducing the number of bacterial contaminants to a predetermined safe level. Disinfecting generally means destroying pathogenic and other types of microorganisms, while sterilizing can be more extensive in that it kills all microbial forms and/or include destroying the ability of the microbial forms to reproduce.

Ultraviolet radiation, which can be used interchangeably with ultraviolet light, means electromagnetic radiation having a wavelength ranging from approximately 10 nm to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm.

Generally, ultraviolet radiation, and in particular, UV-B radiation and UV-C radiation is "germicidal," i.e., it deactivates the DNA of bacteria, viruses and other pathogens, and thus, destroys their ability to multiply and cause disease. This effectively results in sterilization of the microorganisms. Specifically, UV-B radiation and UV-C radiation cause damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. Ultraviolet radiation with a wavelength of approximately between about 250 to about 280 nm provides the highest germicidal effectiveness, while an ultraviolet radiation between about 260 nm to about 310 nm is sufficient for providing overall germicidal effectiveness of medical devices and equipment. While susceptibility to ultraviolet radiation varies, exposure to ultraviolet energy in the above range for about 20 to about 34 milliwatt-seconds/cm$^2$ is adequate to deactivate approximately 99 percent of the pathogens.

As used herein, a material/structure is considered to be "reflective" to ultraviolet light of a particular wavelength when the material/structure has an ultraviolet reflection coefficient of at least 30 percent for the ultraviolet light of the particular wavelength. A highly ultraviolet reflective material/structure has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through. Also, unless otherwise noted, the term "set" means one or more (i.e., at least one) and the phrase "any solution" means any now known or later developed solution.

Turning to the drawings, FIG. 1 shows a schematic of a cross-sectional view of an ultraviolet medical device illuminator 100 coupled to a medical device 102 according to an embodiment. In FIG. 1, the medical device 102 is a stethoscope having a chest piece 104 with a diaphragm 106 and a bell 108 each having an outer contacting surface 109. A tubing 110 connects the chest piece 104 to a binaural assembly (e.g., ear tips and ear tubes) which is not shown for clarity. The bell 108 of the stethoscope is typically cup-shaped and can be placed in contact with a patient and used to listen to low-pitch sounds via the binaural assembly, while the diaphragm 106, which is flat and drum-like, can be used to listen to high-pitched sounds.

Although the medical device 102 in FIG. 1 is a stethoscope as is most of the embodiments described herein, the ultraviolet medical device illuminator and the accompanying ultraviolet cleaning treatment system and embodiments thereof, as described herein, are suitable for use with other medical devices and instruments containing similarly size elements that may need a cleaning treatment. For example, a medical probe instrument, such as for example, an ultrasound probe, which is described below with reference to FIGS. 7A-7B, is suitable for use with an ultraviolet medical device illuminator and accompanying ultraviolet cleaning treatment system described herein. Other possible medical devices, instruments and equipment that have applicability with an ultraviolet medical device illuminator and accompanying ultraviolet cleaning treatment system can include, but are not limited to other devices that have a surface comparable in size and shape to the surface of a stethoscope such as, for example, dental equipment.

Referring back to FIG. 1, the ultraviolet medical device illuminator 100 can include an open-ended housing 112 having a cavity 114 formed therein that is configured to receive the medical device 102. As shown in FIG. 1, the housing 112 can have an outer rim 116 on the open side of the housing that extends beyond the cavity 114. The outer rim 116 of the housing 112 can be used to accommodate the chest piece 104. In one embodiment, the diaphragm 106 can be positioned against the open side of the housing 112 such that an outer edge portion 118 of the diaphragm 106 sits in the outer rim 116 of the housing 112 with the outer contacting surface 109 in substantial alignment with the opening into the cavity 114.

Although not shown, the outer rim 116 of the housing 112 can further include a fastener mechanism to aid in securely fastening the outer edge portion 118 of the diaphragm 106 and the outer edge portion 120 of the bell 108. In one embodiment, the fastener mechanism can include a magnetic coupling that can magnetically attach to a metal strip on the outer edge portion 118 of the diaphragm 106 and the outer edge portion 120 of the bell 108. Other fastener mechanisms can include, but are not limited to, clips, tabs, hook and loop fasteners, mechanical fasteners (e.g., threaded connections), friction type fastening devices placed between two surfaces, etc.

Although FIG. 1 shows the outer edge portion 118 of the diaphragm 106 positioned against the open side of the housing 112, it is understood that an outer edge portion 120 of the bell 108 can be positioned to sit in the outer rim 116 of the housing 112. For example, the housing 112 could include an expandable and compressible material, such as an elastomer, to accommodate the varying sizes between the outer edge portions of the diaphragm 106 and the bell 108. Other materials can include, for example, rubber having an internal surface with an ultraviolet reflective property, e.g., through deposition of aluminum thereon. In this manner, the outer contacting surface 109 of either the diaphragm 106 or the bell 108 could be positioned to be in substantial alignment with the opening into the cavity 114 once either end of the chest piece 104 is coupled with the outer rim 116 of the housing 112. In this embodiment, the outer rim 116 of the housing 112 could also be configured with one of the aforementioned fastener mechanisms to aid in securing either the diaphragm 106 or the bell 108.

The ultraviolet medical device illuminator 100 can also be configured with a connector 122 that secures the illuminator to the medical device 102. For example, the ultraviolet medical device illuminator 100 can include a retractable tether that fastens to the medical device 102. In one embodiment, the tether can be secured to the tubing 110 of the stethoscope. In this manner, the chest piece 104 can easily be removed from the ultraviolet medical device illuminator 100 when needed for an examination. After the examination, the ultraviolet medical device illuminator 100 can then be secured back to the stethoscope. It is understood that other forms of connectors can be used to secure the ultraviolet medical device illuminator 100 to the medical device 102. Other possible connectors can include, but are not limited to, cords, rope, chains, suction cup(s), and/or the like.

FIG. 1 shows that the ultraviolet medical device illuminator 100 can have at least one ultraviolet radiation source 124 located within the cavity 114 of the housing 112, adhering to an inner surface 126, that forms part of an ultraviolet cleaning treatment system. Each ultraviolet radiation source 124 is configured to emit ultraviolet radiation towards a surface of the medical device 102 to effectuate a cleaning treatment. In the example illustrated in FIG. 1, each ultraviolet radiation source 124 is configured to emit ultraviolet radiation within the cavity 114 that is directed to the outer contacting surface 109 of the diaphragm 106 to provide a cleaning treatment of the surface. The set of ultraviolet radiation sources 124 can comprise any combination of one or more ultraviolet radiation emitters. Examples of ultraviolet radiation emitters can include, but are not limited to, high intensity ultraviolet lamps (e.g., high intensity mercury lamps), discharge lamps, UV LEDs, super luminescent LEDs, laser diodes, and/or the like. In one embodiment, the set of ultraviolet radiation sources 124 can include a set of LEDs manufactured with one or more layers of materials selected from the group-III nitride material system (e.g., $Al_xIn_yGa_{1-X-Y}N$, where $0 \le x$, $y \le 1$, and $x+y \le 1$ and/or alloys thereof). Additionally, the set of ultraviolet radiation sources 124 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures include, but are not limited to, a waveguide, a plurality of ultraviolet fibers, each of which terminates at an opening, a diffuser, and/or the like.

It is understood that the number of ultraviolet radiation sources 124 illustrated in FIG. 1 is only illustrative. Those skilled in the art will appreciate any number of ultraviolet radiation sources 124 may be located within the cavity 114 along the inner surface 126. For example, the ultraviolet medical device illuminator 100 can have only one ultraviolet radiation source 124 or multiple ultraviolet radiation sources 124 can be located at the same position along the inner surface 126 (e.g. a central portion) or at varying locations.

In order to effectuate a cleaning treatment of an outer contacting surface 109 of the medical device 102, the ultraviolet radiation sources 124 can be configured to be operated at a number of wavelengths. For example, in one embodiment, the ultraviolet radiation sources 124 can be configured to operate at a wavelength that ranges from about 260 nm to about 310 nm. Emission of ultraviolet light within this range for a predetermined time period is sufficient to effectively clean the medical device 102 from a germicidal effectiveness point of view.

In one embodiment, the ultraviolet radiation sources 124 can be configured to function in a coordinated manner. For example, the ultraviolet radiation sources 124 can operate at the same wavelengths and intensities for the same duration, or the sources can operate at different wavelengths and intensity for varying durations. In one embodiment, a first set of ultraviolet radiation sources 124 can operate at a target wavelength and intensity that is designed for the disinfection of one type of bacteria and/or viruses, while a second set of ultraviolet radiation sources 124 can operate at a different target wavelength and intensity that is designed for disinfection of a different type of bacteria and/or viruses.

In order to recycle or recirculate the ultraviolet radiation emitted from the ultraviolet radiation sources 124, all of the inner surface 126 of the cavity 114 or at least a portion thereof can have an ultraviolet reflective layer formed on an ultraviolet impenetrable material that surrounds the cavity. This also includes the portion of the inner surface 126 of the cavity 114 that is proximate the outer rim 116 of the housing 112 that accommodates the outer edge portions 118, 120 of the chest piece 104 of the stethoscope. An ultraviolet reflective layer with a reflection coefficient of at least 50% will enable recycling of the ultraviolet radiation generation from the ultraviolet radiation sources 124. In one embodiment, the ultraviolet reflective layer can include a diffusive ultraviolet reflective layer. The diffusive ultraviolet reflective layer can include a coating or thin film of a fluoropolymer. Examples of a fluoropolymer that are suitable as an ultraviolet reflective material that enables diffusive reflectivity can include, but are not limited to, expanding polytetrafluoroethylene (ePTFE) membrane (e.g., GORE® DRP® Diffuse Reflector Material), polytetrafluoroethylene (PTFE), and/or the like.

Although not shown in detail in FIG. 1, in addition to the ultraviolet medical device illuminator 100, the ultraviolet cleaning treatment system can include a multitude of components that enable the illuminator 100 to effectuate a cleaning treatment of a medical device 102, such as the stethoscope depicted in this figure. For example, the ultraviolet cleaning treatment system can include a control unit 128 that determines whether the medical device 102 needs a cleaning treatment in response to the medical device being secured to the housing 112. In the embodiment depicted in FIG. 1, the control unit 128 in conjunction with a set of sensors 130 located within the cavity 114 of the housing 112, adhering to the inner surface 126, can determine when the outer edge portion 118 of the diaphragm 106 is placed in the outer rim 116 of the housing 112. In one embodiment, one of the sensors 130 depicted in FIG. 1 can include a pressure sensor, a proximity sensor (e.g., a capacitance, optical, magnet proximity sensor), or the like that detects when the outer edge 118 of the diaphragm 106 is positioned in the outer rim 116 of the housing 112. For example, a pressure sensor can measure the pressure experienced by the outer rim 116 of the housing 112, while a proximity sensor can determine the proximity of the outer edge 118 of the diaphragm 106 to the outer rim 116 of the housing 112. In either case, the set of sensors 130 would generate signals representative of the conditions that each are configured to detect and send those signals to the control unit 128 which determines when the outer edge 118 of the diaphragm 106 is secure within the outer rim 116 of the housing 112.

The control unit 128 can instruct another one of the sensors 130, which is configured to determine whether the contacting surface 109 of the diaphragm 106 needs a cleaning treatment. In one embodiment, a bacterial fluorescence sensor can detect the amount or presence of bacteria, germs, viruses, and/or the like, which is present on the contacting surface 109 of the diaphragm 106. In particular, the bacterial fluorescence sensor generates signals representative of the condition of the contacting surface 109 with respect to the amount of bacteria, germs, viruses, and the like, and sends those signals to the control unit 128. The control unit 128 can determine whether a cleaning treatment is necessary as a function of the signals provided by the bacterial fluorescence sensor using any solution.

In one embodiment, the control unit 128 can activate the operation of the ultraviolet radiation sources 124 in response to determining that the contacting surface 109 of the diaphragm 106 has an amount of bacteria, germs, viruses, and/or the like, which exceeds a predetermined threshold, and thus, requires a cleaning treatment. Activating the operation of the ultraviolet radiation sources 124 by the control unit 128 can include specifying a plurality of operating parameters for the cleaning treatment of the medical device (e.g., the stethoscope). In one embodiment, the plurality of operating parameters can include a cleaning treatment time that the ultraviolet radiation sources 124 emit the ultraviolet radiation towards the surface of the medical device (e.g., contacting surface 109 of the diaphragm 106), a dosage of ultraviolet radiation delivered by the ultraviolet radiation sources 124, a power setting for operating the ultraviolet radiation sources 124, and a maximum operating temperature for the cleaning treatment. It is understood that these operating parameters are illustrative of some of the parameters that can be set by the control unit 128 and is not meant to be limiting as other parameters exist which may be specified such as a disinfection time, a wavelength of the ultraviolet light used for disinfection, and/or the like.

Furthermore, it is understood that the sensors 130 can include a multitude of different types of sensors and that the various embodiments of the present invention are not meant to be limited to a bacterial fluorescence sensor, a pressure sensor, and a proximity sensor. Other sensors that are suitable for use with the ultraviolet cleaning treatment system can include, but are not limited to, a temperature sensor, a chemical sensor, and a radiation sensor (e.g., an ultraviolet dose counter or meter), etc. Each of these sensors could detect the level or amount of a particular parameter that each is intended to measure and send signals thereof to a control unit 128. For example, a temperature sensor can detect the temperature within the cavity 114 and/or the temperature of the surface of the medical device 102 (e.g., a contacting surface 109 of the diaphragm 106), a chemical sensor can detect a level of a particular chemical that resides on a surface be irradiated with the ultraviolet radiation, and a radiation sensor can detect a level of radiation that is present in the cavity 114. These sensors 130 along with any of the aforementioned fluorescence, pressure, and proximity sensors can be deployed along with the ultraviolet radiation sources 124 in any desired configuration. For example, the sensors 130 can be interspersed with the ultraviolet radiation sources 124 or separated from each other.

The control unit 128 can include a timer with switches and/or the like, to manage the duration that the ultraviolet radiation sources 124 are on for a particular cleaning treatment and ensure that radiation is applied to a particular surface of the medical device 102 for that duration. In one embodiment, the control unit 128 operating in conjunction with the timer can manage the amount of time that the ultraviolet radiation sources 124 radiate in the UV-C range versus the UV-B range. The duration and frequency treatment that the ultraviolet radiation sources 124 are utilized can depend on detected condition signals provided to the control unit 128 by any of the sensors 130, as well as any other predetermined treatment factors such as the length that a particular medical device has been used, areas of contact when in use, and whether a set predefined treatment schedule is being followed.

During operation of a cleaning treatment, the control unit 128 can be used to control at least one of a plurality of predetermined ultraviolet radiation characteristics associated with the ultraviolet radiation emitted from the ultraviolet radiation sources 124. The predetermined ultraviolet radiation characteristics that can be controlled by the control unit 128 can include wavelengths, intensities, and durations and/or the like. In one embodiment, the control unit 128 can control the wavelength of ultraviolet radiation and intensity spatially over a surface of the medical device 102. As an example, the control unit 128 can control the ultraviolet radiation sources 124 to operate at a target wavelength and intensity for a duration that is designed for the disinfection of bacteria and/or viruses on a surface of a medical device (e.g., outer contacting surface 109 of the diaphragm 106).

In an embodiment, the control unit 128 can determine the target intensity of the radiation based on an amount of time since a previous cleaning has been performed. For example, the control unit 128 can implement an algorithm in which a minimum ultraviolet intensity is utilized when a previous cleaning was performed within a certain period of time and the intensity is increased to a maximum intensity, which is utilized when the previous cleaning was performed over a maximum period of time. The intensity range can be determined based on attributes of the ultraviolet radiation sources 124. The target intensity can be incremented in steps or continuously over the range of times corresponding to the varying intensities. The range of times can be determined based on, for example, feedback data acquired regarding a severity of contamination typical for a period of time. In an embodiment, the control unit 128 can generate a warning signal for presentation to a user when the time period since a previous cleaning has exceeded a maximum recommended time (e.g., time period corresponding to the maximum ultraviolet radiation). The warning signal can be generated using any type of output device including, for example, a vibration device, a visible light (e.g., flashing), an auditory signal generated by a speaker, and/or the like.

In addition, during the operation of the cleaning treatment, the control unit 128 can be used to turn on or off the ultraviolet radiation sources 124 dependent upon the detected conditions provided by the sensors 130. In one embodiment, the control unit 128 can turn on or off each of the ultraviolet radiation sources 124 via an actuator. Also, the control unit 128 can be used to adjust one or more of the ultraviolet radiation characteristics based on the conditions detected by the sensors 130. For example, the control unit 128 can use the signals from a bacterial fluorescence sensor that are representative of the amount of bacteria, germs, viruses, and/or the like, present on a surface of the medical device to adjust the intensity, the wavelength, the duration and or the pattern of the ultraviolet radiation emitted from any of the ultraviolet radiation sources 124. In another embodiment, the control unit 128 can be configured to interrupt the operation of the ultraviolet radiation sources 124 in response to receiving temperature signals from a temperature sensor and determining that the temperature of the cleaning treatment has exceeded the maximum temperature. The control unit 128 can resume the cleaning treatment after a predetermined cooling time has elapsed.

The control unit 128 can also include a wireless transmitter and receiver that is configured to communicate with a remote location via WiFi, BLUETOOTH, and/or the like. As used herein, a remote location is a location that is apart from the ultraviolet cleaning treatment system. For example, a remote computer can be used to transmit operational instructions to the wireless transmitter and receiver. The operational instructions can be used to program functions performed and managed by the control unit 128. In another embodiment, the wireless transmitter and receiver can transmit cleaning treatment results, data from the sensors 130 to the remote computer, to facilitate maintenance and diagnostic operations on the ultraviolet cleaning treatment system.

The control unit 128 can include an input component and an output component to allow a user to interact with the ultraviolet medical device illuminator 100 and the control unit 128, and to receive information from the illuminator and the treatment system. In one embodiment, the input component can permit a user to adjust at least one of the aforementioned plurality of operating parameters. This can include making adjustments during the cleaning treatment operation and/or prior to initiating a treatment. In one embodiment, the input component can include a set of buttons and/or a touch screen to enable a user to specify various input selections regarding the operating parameters as well as the cleaning treatment. In one embodiment, the output component can include a visual display for providing status information on the cleaning treatment (e.g., time remaining, the presence of bacteria, viruses, germs or the like), an indication that a cleaning treatment is recommended, an indication that the device has been sterilized, disinfected, sanitized, an indication that the device has been disinfected, sanitized, an indication after its last use, a simple visual indicator that displays whether a cleaning treatment is underway (e.g., an illuminated light) or if the treatment is over (e.g., absence of an illuminated light).

The ultraviolet cleaning treatment system can further include a power source that is configured to power each of the ultraviolet radiation sources 124, the control unit 128 and the sensors 130. In one embodiment, the power source can take the form of one or more batteries, a vibration power generator that can generate power based on magnetic inducted oscillations or stresses developed on a piezoelectric crystal. In another embodiment, the power source can include a super capacitor that is rechargeable. Other power components that are suitable for use as the power source for the ultraviolet medical device illuminator 100 and the control unit 128 can include a mechanical energy to electrical energy converter such as a piezoelectric crystal, and a rechargeable device.

Figure 8:
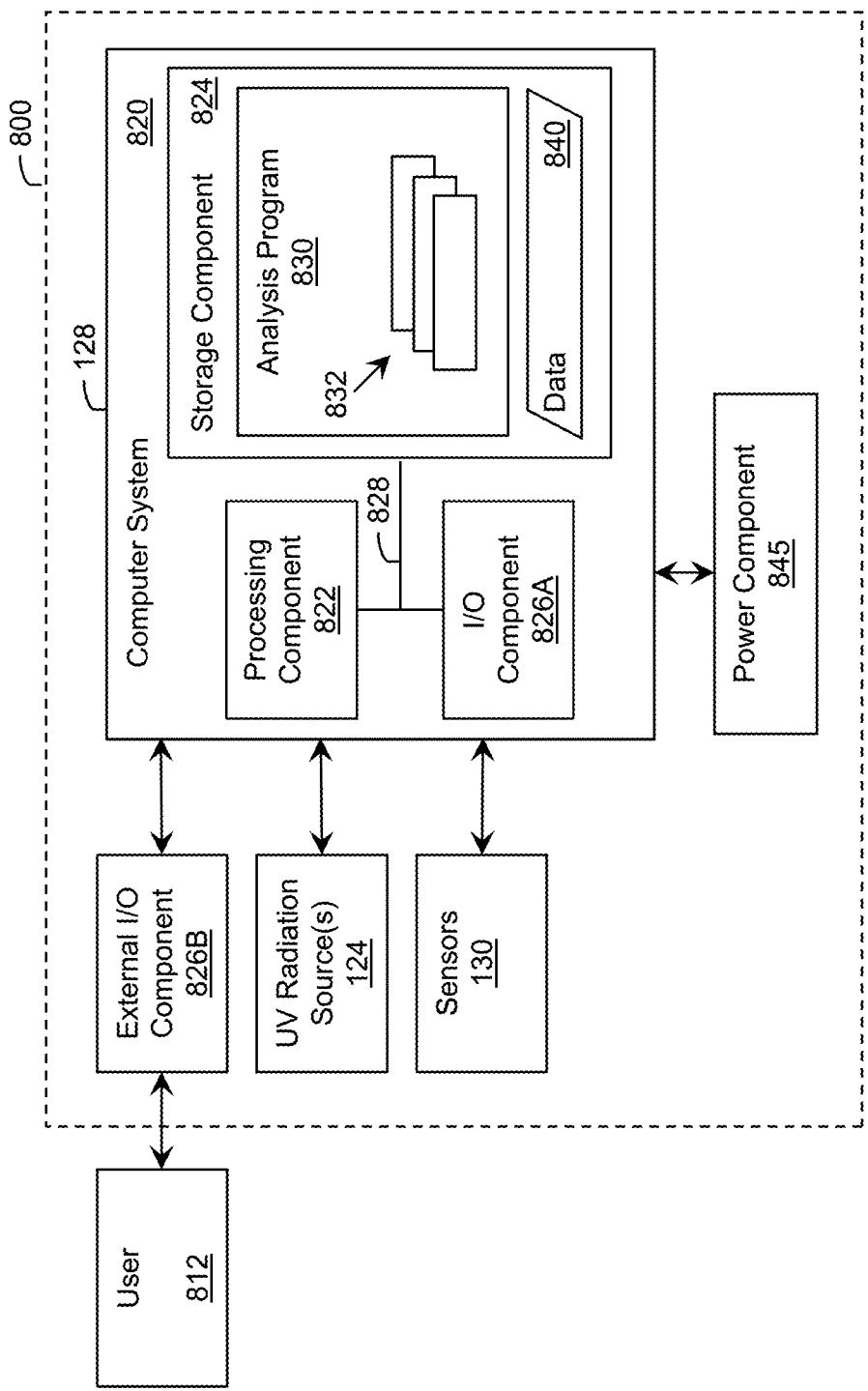
FIG. 8 shows a schematic of an ultraviolet cleaning treatment system that can be implemented with any of the ultraviolet medical device illuminators depicted in FIGS. 1-7 according to an embodiment.
Figure 9:
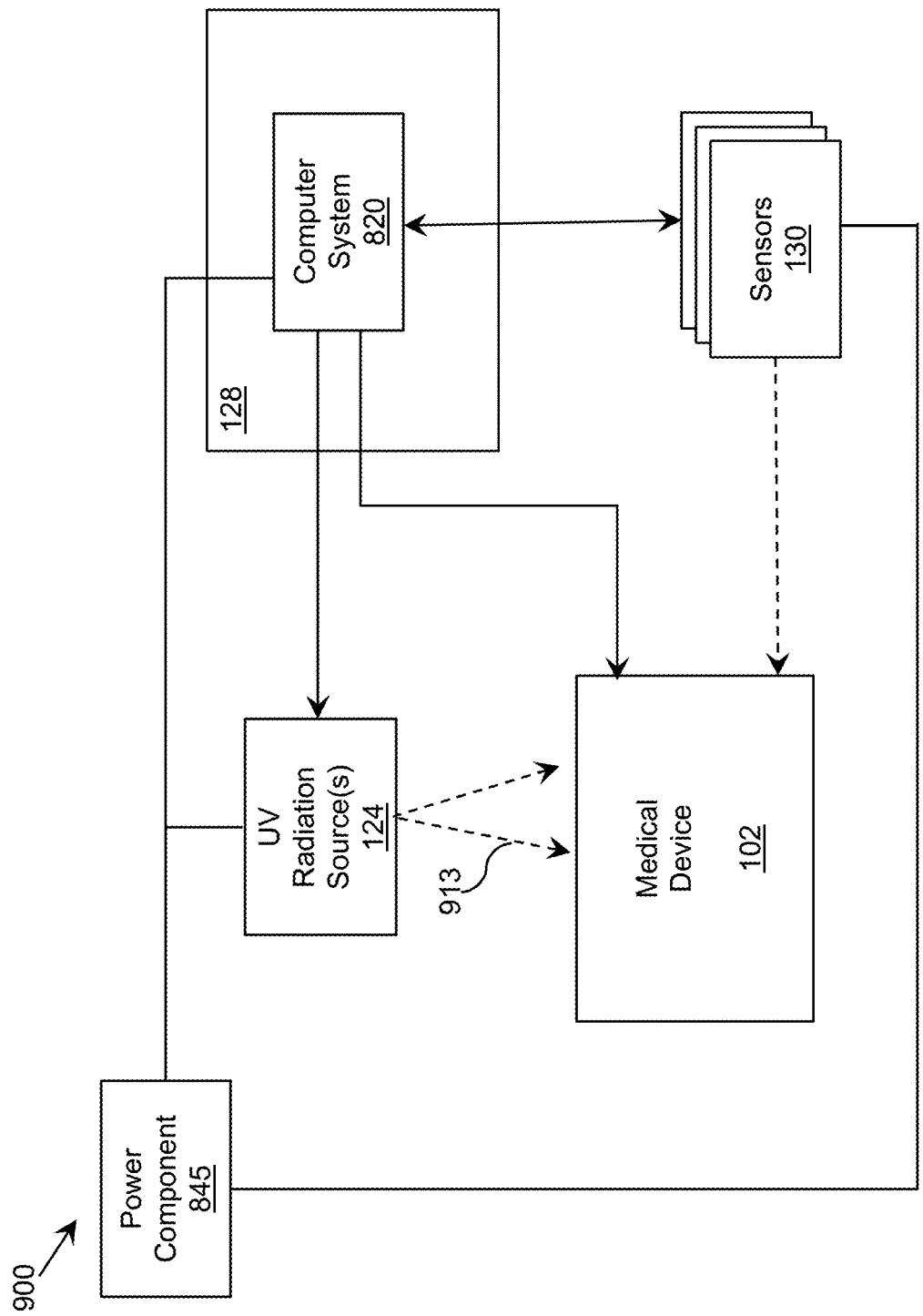
FIG. 9 shows a schematic of an illustrative environment in which the ultraviolet-cleaning treatment system depicted in FIG. 8 can be used to facilitate a cleaning treatment of a medical device according to an embodiment.

The aforementioned components of the ultraviolet cleaning treatment system are illustrated in FIGS. 8-9 and discussed further with regard to these figures. These components of the ultraviolet cleaning treatment system are suitable for use with the various other ultraviolet medical device illuminators described herein with respect to FIGS. 2-7. It is understood that the functions of these components can vary and will depend on the type medical device that is to undergo a cleaning treatment and the environment in which the device is used. Thus, the functions described are only illustrative of examples of particular functions and operations to be performed and are not meant to be limiting to the embodiment of FIG. 1 as well as to an ultraviolet cleaning treatment system used in conjunction with the embodiments pertaining to FIGS. 2-7.

In order to complement the use of the ultraviolet medical device illuminator 100 and the accompanying ultraviolet cleaning treatment system in a medical examination environment, the medical device 102 can be configured with a visible light source 132 such as an LED. For example, in FIG. 1, the chest piece 104 of the stethoscope can be configured with a visible light source that can be used during an examination of a patient. In one scenario, the visible light source 132 can be used to improve the placement of the stethoscope on a patient's body, allowing a user to examine a skin condition of the patient prior to placing the stethoscope on the patient.

Other electronic elements can be incorporated with the medical device illuminator 100 in order to provide a better medical examination environment. For example, the medical device illuminator 100 can include recording electronic elements that record transcription, an imaging device capable of acquiring image data, a thermometer, and communication elements such as wireless elements that send the recorded text, pictures, temperature data and other data pertaining to the cleaning treatment to a computer system including a storage component.

FIGS. 2A-2B show schematics of cross-sectional views of an ultraviolet medical device illuminator 200 in which the ultraviolet radiation sources 124, the sensors 130, and the ultraviolet cleaning treatment system 128 are integrated with a medical device 102 according to an embodiment. The medical device 102 in FIGS. 2A-2B can be a stethoscope that operates as a self-cleaning stethoscope. In this embodiment, the medical device illuminator 200 can include a covering cap 205 that serves as a housing or cover for the chest piece 104 of the medical device 102. The covering cap 205 can have a main body portion 210 and an outer rim portion 215 extending outward from the main body portion 210. In an embodiment where the medical device is a stethoscope, the outer rim portion 215 of the covering cap 205 can be used to be secured to the chest piece 104. In particular, the outer rim portion 215 can be used to secure the diaphragm 106 and the bell 108. FIGS. 2A-2B show the covering cap 205 secured to the diaphragm 106 such that the outer edge portion 118 of the diaphragm 106 abuts against the outer rim 215. Although not shown, the covering cap 205 could also be secured to the bell 108 such that the outer edge portion 120 of the bell 108 abuts against the outer rim 215.

In one embodiment, the outer rim portion 215 of the covering cap 205 can further include a fastener mechanism to aid in securely fastening the outer edge portion 118 of the diaphragm 106 and the outer edge portion 120 of the bell 108. In one embodiment, the fastener mechanism can include a magnetic coupling that can magnetically attach to a metal strip on the outer edge portion 118 of the diaphragm 106 and the outer edge portion 120 of the bell 108. Other fastener mechanisms can include, but are not limited to, clips, tabs, hook and loop fasteners, mechanical fastener (e.g., threaded connections), and/or the like.

Although FIGS. 2A-2B show the outer rim portion 215 of the covering cap 205 covering the diaphragm 106, it is understood that the outer edge portion 120 of the bell 108 can be covered by the outer rim portion 215 of the cap. In this embodiment, the outer rim portion 215 of the covering cap 205 and the outer edge portion 120 of the bell 108 could also be configured with one of the aforementioned fastener mechanisms to aid in securing the bell 108.

In one embodiment, the covering cap 205 could include an expandable and compressible material, such as an elastomer, to accommodate the varying sizes between the outer edge portions of the diaphragm 106 and the bell 108 and cover each one. Other materials can be used for the covering cap 205 besides an elastomer. For example, the covering cap 205 can include any type of material that is ultraviolet absorbing such as, for example, plastic, glass, metal, wood, and/or the like.

As shown in FIGS. 2A-2B, the ultraviolet radiation sources 124, the sensors 130 and the control unit 128 can be integrated within the chest piece 104. For example, the ultraviolet radiation sources 124 can be configured to emit the ultraviolet radiation to a back surface of the outer contacting surface 109 of the diaphragm 108, while the sensors 130 can be configured to obtain various measurements such as those mentioned above during a cleaning treatment operation. The control unit 128 can use the measurements to control the cleaning treatment operation. It is understood, the cleaning treatment system can include some or all of the same components as described herein and operate to perform those noted functions.

In order to facilitate the ultraviolet based cleaning treatment provided in FIGS. 2A-2B, a portion 220 of the medical device 102 can include an ultraviolet transparent material with an ultraviolet transparent window through which the ultraviolet radiation emitted from the ultraviolet radiation sources 124 passes towards a back side of the outer contacting surface 109. In the examples illustrated in FIGS. 2A-2B in which a stethoscope is the representative medical device, a select region of the chest piece 104 can include the ultraviolet transparent material and the ultraviolet transparent window. For clarity, the portion 220 is only illustrated with respect to emitting ultraviolet radiation to a back side of the outer contacting surface 109 of the diaphragm 106. It is understood, that a similar region could be implemented with ultraviolet transparent material and a window along with the ultraviolet radiation sensor 124 and sensors 130 for facilitating a cleaning treatment of a back side of the outer contacting surface 109 of the bell 108.

In one embodiment, the ultraviolet transparent material can include an ultraviolet transparent fluoropolymer. Examples of an ultraviolet transparent fluoropolymer material can include, but are not limited to, fluorinated ethylene propylene co-polymer (EFEP), fluorinated ethylene propylene (FEP), polytetrafluoroethylene (PTFE), ethylene chlorotrifluoroethylene (ECTFE), polychlorotrifluoroethylene (PCTFE), perfluoroalkoxy (PFA), polyvinylidene fluoride (PVDF), ethylene tetrafluoroethylene (ETFE), tetrafluoroethylene hexafluoropropylene vinylidene fluoride co-polymer (THV), low density polyethylene (LDPE), perfluoro methyl alkoxy (MFA), and/or the like. While primarily described in conjunction with fluoropolymers, it is understood that other comparable materials can be utilized such as polylactide (PLA), fused silica, sapphire, THE, and/or the like.

Even though the back side of the outer contacting surface 109 as illustrated in the embodiments of FIGS. 2A-2B, is irradiated with the ultraviolet radiation, the front side of this surface of either the diaphragm 106 or the bell 108 will be effectively sterilized, disinfected, or sanitized, because the ultraviolet radiation will penetrate the ultraviolet transparent material forming the outer contacting surface 109. In this manner, the ultraviolet medical illuminator 200 can enable the medical device 102 to become a self-cleaning device.

FIGS. 2A-2B show that there are multiple possible configurations for implementing the ultraviolet radiation sources 124, the sensors 130 and the control unit 128. As noted above, the amount and location of the ultraviolet radiation sources 124, the sensors 130 and the control unit 128 can vary. For example, in FIG. 2B, the ultraviolet radiation sources 124 can be integrated within an outer edge portion 118, 120 of one of the diaphragm 106 and the bell 108, and configured to emit the ultraviolet radiation at a shallow angle to one of surfaces of the diaphragm and the bell. Having the ultraviolet radiation sources 124 in the outer edge portion 118, 120 of one of the diaphragm and the bell to emit the ultraviolet radiation at a shallow angle serves to increase an illumination intensity over the outer contacting surface 109. In one embodiment, the shallow angle that can be used to direct ultraviolet radiation from an outer edge portion 118, 120 can include any angle formed with a normal of one of the diaphragm 106 and the bell 108 that is larger than 45 degrees.

Figure 3:
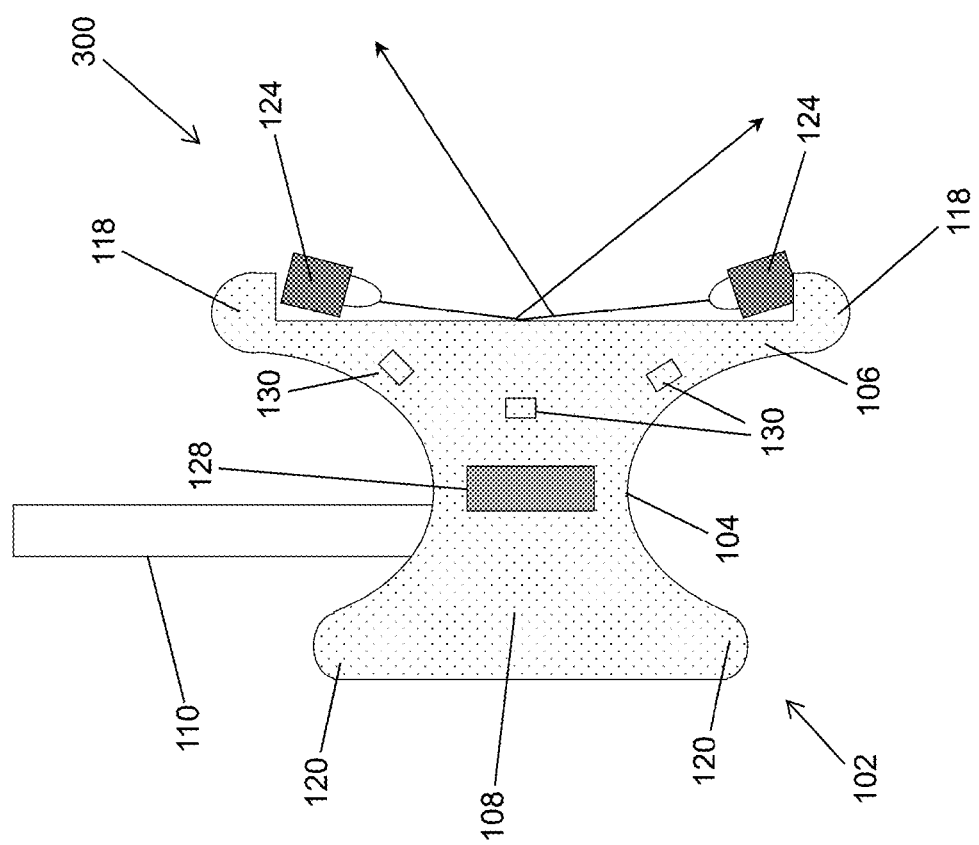
FIG. 3 shows a schematic of a cross-sectional view of an ultraviolet medical device illuminator in which ultraviolet radiation sources are integrated with a medical device to facilitate usage as a wand cleaning treatment instrument according to an embodiment.

FIG. 3 shows a schematic of a cross-sectional view of an ultraviolet medical device illuminator 300 in which the ultraviolet radiation sources 124 are integrated with a medical device 102, like in FIG. 2B, but in this embodiment there is no covering cap. In particular, the ultraviolet radiation sources 124 are integrated within the outer edge portion 118 of the diaphragm 106 and are configured to emit ultraviolet radiation at a shallow angle, while the control unit 128 and the set of sensors 130 are integrated in the chest piece 104.

Although not shown in FIG. 3, it is understood that the ultraviolet radiation sources 124 could also be incorporated within the outer edge portion 120 of the bell 108, and the set of sensors 130 could be deployed in the bell to obtain operational data during a cleaning treatment.

In the embodiment depicted in FIG. 3, the medical device illuminator 300 can be used as a wand cleaning treatment instrument that can provide a cleaning treatment to the surfaces of a wide variety of objects. That is, the ultraviolet radiation sources 124, the sensors 130 and the control unit 128 can be used to generate ultraviolet radiation to provide an ultraviolet based cleaning treatment to a surface that is contaminated. For example, a user could use the wand clean treatment instrument to clean an examining table used for examining a patient, or a counter on which a user sets equipment, papers, and/or the like, while visiting with a patient. The scenarios in which the wand clean treatment instrument could be used are numerous. Furthermore, the wand clean treatment instrument has application beyond a medical setting. For example, the wand clean treatment instrument could be used in an industrial setting, an educational setting, a business setting, and the like.

In addition to having components that function in the above-mentioned manner, the control unit 128 could be configured with components that enable the medical device illuminator 300 to operate as a wand clean treatment instrument. In one embodiment, the control unit 128 can be configured to override the cleaning treatment in response to receiving an input command from the user via an input component of the control unit 128 that the user desires to use the medical device as a wand cleaning treatment instrument. In this manner, the control unit 128 can permit the user to use the medical as the wand cleaning treatment instrument in response to determining that predetermined safety requirements have been satisfied such as, for example, minimizing exposure to ultraviolet radiation by the patient and medical personnel.

The control unit 128 can specify one or more predetermined wand cleaning treatment operating parameters for cleaning a particular surface. These predetermined wand cleaning treatment operating parameters can include, but are not limited to, a cleaning treatment time that the ultraviolet radiation sources 124 emit the ultraviolet radiation towards a surface, a dosage of ultraviolet radiation delivered by the ultraviolet radiation sources 124, a power setting for operating the ultraviolet radiation sources 124, a maximum operating temperature for the cleaning treatment for the wand cleaning treatment instrument, and/or the like. In addition, the control unit 128 can control at least one of a plurality of predetermined ultraviolet radiation characteristics associated with the ultraviolet radiation emitted from the ultraviolet radiation sources 124 during the wand cleaning, such as wavelengths, intensities, and durations and/or the like. As discussed herein, a user can use the input component to adjust these characteristics during the wand cleaning treatment, or the control unit 128 can implement any such changes based on measurements received by any one of the aforementioned sensors 130 that could be implemented with the medical device illuminator 300.

Figure 4:
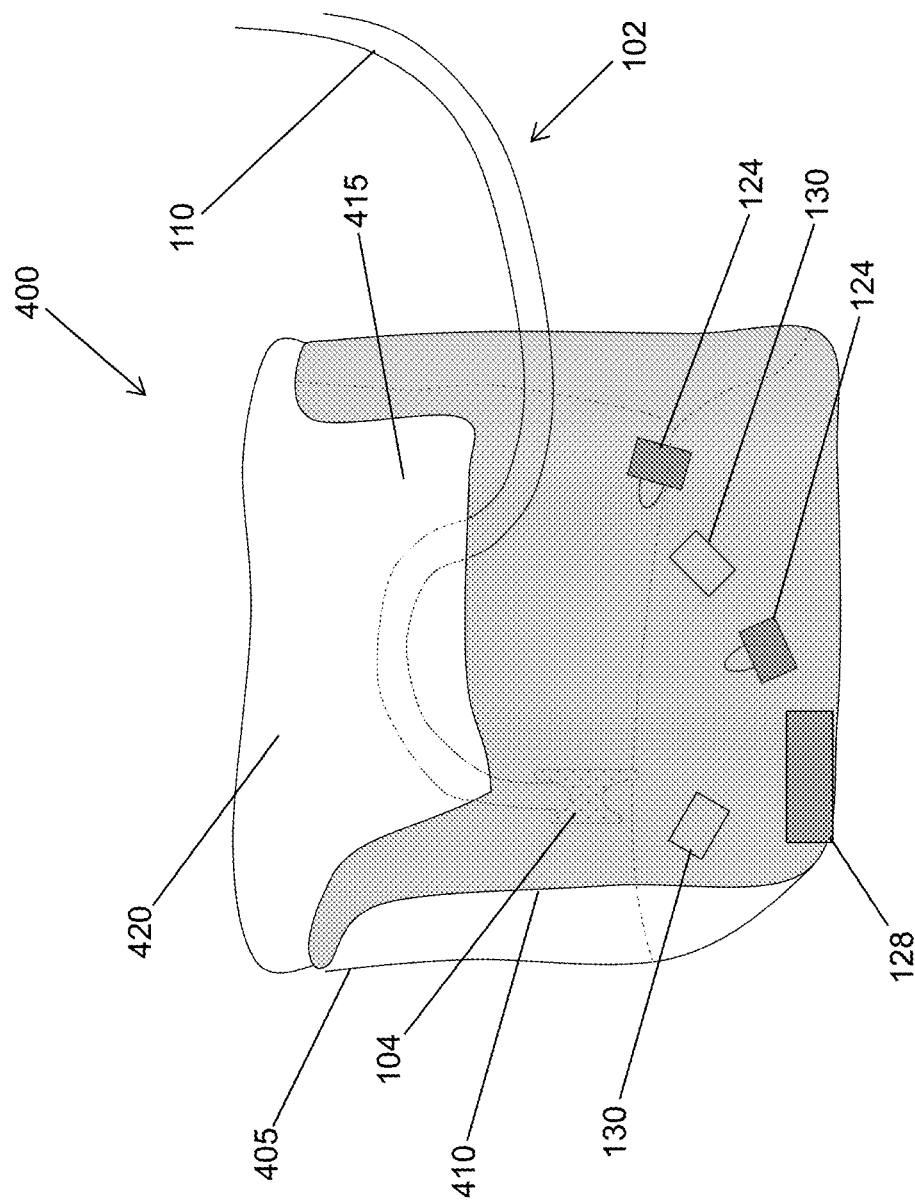
FIG. 4 shows a schematic of an ultraviolet medical device illuminator in the form of a medical device cleaning container according to an embodiment.

FIG. 4 shows a schematic of an ultraviolet medical device illuminator 400 in the form of a medical device cleaning container 405 according to an embodiment. In one embodiment, the medical device cleaning container 405 can include a flexible receptacle or pouch 410 having an opening 415 to a reflective inner surface that is at least 30% reflective with a reflection coefficient that is at least 50%, and that receives a medical device 102. The medical device cleaning container 405 can further include an overlapping opening cover 420, which can cover the opening 415 in response to the medical instrument inserted therein to prevent ultraviolet radiation that is emitted from the ultraviolet radiation sources 124 from escaping the receptacle 410 during a cleaning treatment of the medical device 102.

In one embodiment, as illustrated in FIG. 4, the medical device 102 can include a stethoscope. As shown in FIG. 4, the chest piece 104 along with at least part of the tubing 110 can be placed in the receptacle 410 and fastened therein by covering the receptacle with the overlapping opening cover 420. Although not shown in FIG. 4, the binaural assembly of the stethoscope including the ear tips and ear tubes also can be placed in the receptacle 410 and fastened therein by the overlapping opening cover 420. In one embodiment, both the chest piece 104 and the binaural assembly can be placed together in the medical device cleaning container 405.

Once the medical device 102 (or a desired portion thereof) has been inserted in the receptacle 410 of the medical device cleaning container 405 and the overlapping opening cover 420 has been covered, the control unit 128 can administer a cleaning treatment to the chest piece 104 and/or the binaural assembly. Like the other embodiments described herein, the medical device cleaning container 405 of the ultraviolet medical device illuminator 400 can include a multitude of sensors 130 to obtain a variety of measurements before, during and after the cleaning treatment of the medical device 102. For example, in one embodiment, one sensor 130 could include a pressure sensor, a proximity sensor (e.g., a capacitance, optical, magnet proximity sensor), or the like that detects when the medical device 102 has been placed in the receptacle and another similar type of sensor could detect when the opening 415 has been covered by the overlapping opening cover 420.

The control unit 128 can determine when any part or surface of the medical device 102 requires a cleaning treatment. As mentioned above, a bacterial fluorescence sensor can be used to detect the amount or presence of bacteria, germs, viruses, and the like, that is present on the medical device 102. If a cleaning treatment is deemed necessary, the control unit 128 can activate the operation of the ultraviolet radiation sources 124 by specifying any of the plurality of operating parameters for the cleaning treatment of the medical device. An input component of the control unit 128 also can be used to specify and/or adjust the parameters during the cleaning treatment.

As described herein, any one of a multitude of sensors 130 can be configured to obtain measurements from the medical device 102 and/or the interior of the receptacle 410. Examples, include but are not limited to, temperature measurements, chemical measurements, radiation measurements, and/or the like. Depending on the measurements, the control unit 128 can control the operating parameters as well as any of the plurality of predetermined ultraviolet radiation characteristics associated with the ultraviolet radiation emitted from the ultraviolet radiation sources 124.

During the cleaning treatment and after, the output component of the control unit 128 can indicate status information of the cleaning treatment to the user using any solution. As described herein, information provided from an output component of the control unit 128 can include, but is not limited to, status information on the cleaning treatment (e.g., time remaining, the presence of bacteria, viruses, germs or the like), an indication that a cleaning treatment is recommended, an indication that the device has been sterilized, disinfected, sanitized, an indication that the device has been disinfected, sanitized, etc., since its last use, the treatment has been suspended and needs a cool-down period, and/or the like.

It is understood that the embodiment depicted in FIG. 4 represents only one possible configuration for the ultraviolet radiation sources 124, the control unit 128 and the sensors 130 and is not meant to limit the scope of this embodiment. Similarly, it is understood that the medical device cleaning container 405 can take other forms than a receptacle or pouch. Those skilled in the art will appreciate that larger or smaller containers with openings to reflective surfaces that promote the reflectivity of radiation emitted from ultraviolet radiation sources are suitable for use with this embodiment. The size of the container will likely depend on the medical device, instrument or equipment that is placed inside and the amount and types sensors that will be deployed.

Figure 5:
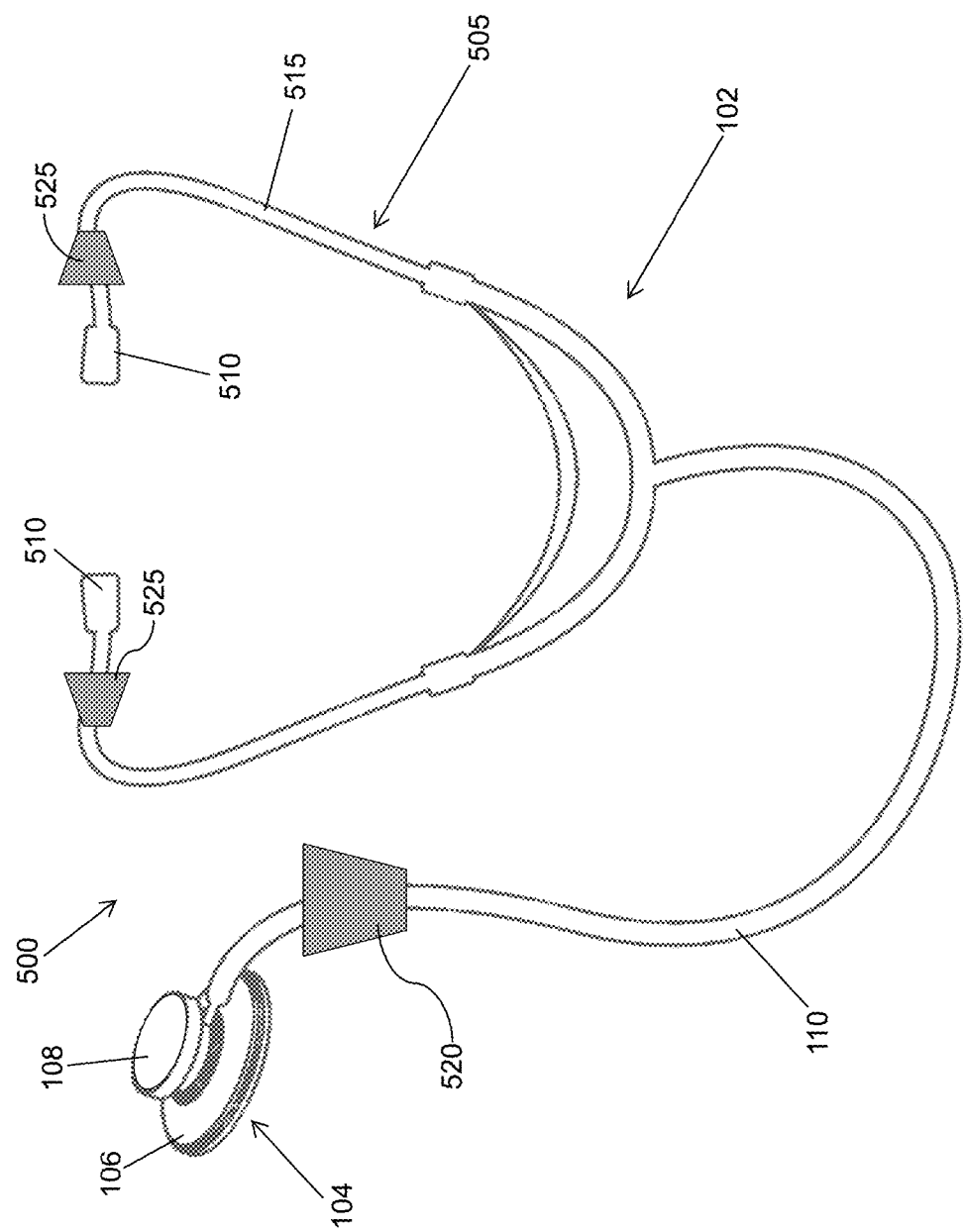
FIG. 5 shows a schematic of an ultraviolet medical device illuminator in the form of slidable units, which accommodate various sized elements of a medical device according to an embodiment.

FIG. 5 shows a schematic of an ultraviolet medical device illuminator 500 in the form of slidable units that accommodate various sized elements of a medical device 102 and provide an ultraviolet cleaning treatment to the device according to an embodiment. In FIG. 5, the medical device 102 can take the form of a stethoscope having a chest piece 104 with a diaphragm 106 and a bell 108 each having an outer contacting surface. A tubing 110 connects the chest piece 104 to a binaural assembly 505 having ear tips 510 and ear tubes 515. It is understood that the use of a stethoscope in this embodiment as a medical device that is suitable for use with the ultraviolet medical device illuminator 500 is only representative of one possible device that can be used, and is not meant to limit the scope of the embodiment. Those skilled in the art will appreciate a modification may be necessary to enable the ultraviolet medical device illuminator 500 to accommodate other medical devices with different shapes and sizes, all of which is considered to be within the scope of the embodiment described herein.

In FIG. 5, the slidable units of the ultraviolet medical device illuminator 500 can include a chest piece housing 520 that can accommodate both the diaphragm 106 and the bell 108 of the chest piece 104 and a pair of binaural assembly housings 525, each of which can accommodate an ear tip 510 of the binaural assembly 505. In particular, the chest piece housing 520 is slidably moveable along the tubing 110 to engage and disengage with the chest piece 104, while the binaural assembly housings 525 are slidably moveable along the ear tubes 515 to engage and disengage with the ear tips 510. Each of the chest piece housing 520 and the binaural assembly housings 525 can include at least one ultraviolet radiation source, sensor, and control unit described herein. In addition, the chest piece housing 520 and the binaural assembly housing 525 can each include a cavity with inner wall surfaces having an ultraviolet reflective layer with a reflection coefficient of at least 50%. In one embodiment, the ultraviolet reflective layer can include a diffusive ultraviolet reflective layer that can include a coating or thin film of a fluoropolymer described herein. Also, the chest piece housing 520 can include a chest piece housing internal fastener that securely fastens the chest piece 104 upon insertion into the chest piece housing 520, and the binaural assembly housing 525 can include a binaural assembly housing internal fastener that securely fastens the ear tips 510 or a portion of the ear tubes 515 upon insertion into the binaural assembly housing 525. In this manner, each fastener inhibits movement during a cleaning treatment.

Details of the chest piece housing 520 and its operation during a cleaning treatment are described further with reference to FIGS. 6A-6B. The explanation is also applicable to the binaural assembly housing 525 except that an ear tip 510 of the binaural assembly would be placed in that housing. Those skilled in the art will appreciate that the binaural assembly housing 525 can also have other features that are applicable for the ear tips 510 and the ear tubes 515 that are placed therein. For example, various optical components can be placed in proximity to the ultraviolet radiation sources 124 within the binaural assembly housing 525 to aid in delivering suitable ultraviolet disinfections to the ear tips 510 during a cleaning treatment. Furthermore, the interior of the binaural assembly housing 525 can have an ultraviolet transparent biofouling material including any of the ultraviolet transparent fluoropolymers described herein to complement the cleaning treatment applied to the outer surfaces of the ear tips 510 during a cleaning treatment.

As shown in FIG. 6A, the chest piece 104 of the stethoscope having an optional visible light source 132 is shown inserted within the chest piece housing 520, while FIG. 6B shows the chest piece 104 housing without the chest piece inserted. In one embodiment, the chest piece 104 is inserted through a cutting 600 formed in a bottom portion 605 of the chest piece housing 520. A chest piece housing internal fastener 610 securely fastens the chest piece 104 in a stable position upon insertion into the chest piece housing 520 through the cutting 600. Any fastener mechanisms (e.g., clips, tabs, magnetic coupling, springs, mechanical fasteners) are suitable for use as the chest piece housing internal fastener 610.

The chest piece housing 520 can include any expandable and compressible material (e.g., elastomer) that can shield ultraviolet radiation from escaping to an ambient environment. Furthermore, as mentioned above, the inner wall surfaces of the chest piece housing 520 can have an ultraviolet reflective layer with a reflection coefficient of at least 50% formed from any fluoropolymer that can serve as a diffusive ultraviolet reflective layer.

The chest piece housing 520 can further include at least one ultraviolet radiation source 124, sensor 130 and the control unit 128. The number and location of the radiation sources 124 and sensors 130 used in the chest piece housing 520 can vary. Similarly, the orientation of the radiation sources 124 and sensors 130 within the chest piece housing 520 can vary. The amount, location and orientation of these components will depend on a number of considerations such as the device being cleaned, the measurements that are desired to be obtained, the type of cleaning, etc.

The control unit 128 can operate in the same manner described herein with respect to other embodiments. In addition, it is understood that the control unit 128 could have the same components as shown and described elsewhere herein, and could operate to perform those noted functions in a like manner within the slidable units (i.e., 520 and 525) of the ultraviolet medical illuminator 500.

As should be apparent from FIGS. 5 and 6A-6B, the slidable units (520 and 525) of the ultraviolet medical illuminator 500 provide a convenient design with small and lightweight sanitizing devices that are adapted for attachment to a stethoscope. Such a design allows the sanitizing device to always be attached to the stethoscope. As a result, a user, such as a health care worker, is always reminded to sanitize at least the chest piece after each use. With this design, the sanitizing devices associated with the chest piece housing 520 can clean both the bell and the diaphragm surfaces of the stethoscope with little effort by sliding the housing 520 on and off the stethoscope chest piece. Similarly, the binaural assembly housing 525 can be used to clean the ear tips and ear tubes by sliding the housing 525 on and off these parts of the binaural assembly. The cutting 600 in the bottom 605 of each housing facilitates quick and effortless insertion and withdrawal of the stethoscope chest piece. In this manner, the chest piece housing 520 and the binaural assembly housing 525 can be slid up the tubing 110 and away from the chest piece 104 and the ear tips 510 when the stethoscope is being used, and slid down to these elements when in use for a cleaning treatment.

FIGS. 7A-7B show schematics of an ultraviolet medical device illuminator 700 that is suitable for use with a medical probe instrument 705 according to an embodiment. In one embodiment, the medical probe instrument 705 can include an ultrasound probe. It is understood that the ultraviolet medical device illuminator 700 is not limited to use with only an ultrasound probe. Instead, the ultraviolet medical device illuminator 700 is suitable for use with any medical probe instrument that is in contact with patients and in need of a periodic cleaning treatment to remove germs, bacteria, viruses, and/or the like, that can form on such instruments after use to prevent their transmission to others. The components that form the ultraviolet medical device illuminator 700 can be scaled to a size to accommodate other medical probe instruments that are different than an ultrasound probe shown herein. Placement and orientation of components such as the ultraviolet radiation sources 124, the sensors 130, and the control unit 128, and the functions performed by these components will depend on several factors including, but not limited to, the size of the probe instrument, the form of cleaning that is desired, and the level and types of germs, bacteria, viruses and the like, that the instrument is susceptible to having.

As shown in FIGS. 7A-7B, the ultraviolet medical device illuminator 700 can include a housing 710 with an opening 715 into a cavity 720 that can accommodate the medical probe instrument 705. In essence, the housing 710 can form a covering, a cap, or container, or the like for retaining the medical probe instrument 705 and applying a cleaning treatment. In one embodiment, the housing 710 can include an ultraviolet impenetrable material, while the cavity 720 can include an inner wall surface having an ultraviolet reflective layer formed on all or at least a portion thereof that facilitates recycling or recirculation of ultraviolet radiation that is emitted from the ultraviolet radiation sources 124 that are located within the walls of the cavity 720 along with one or more sensors 130 in order to increase the efficiency of a cleaning treatment applied to the medical probe instrument 705. The ultraviolet reflective layer can be reflective to at least 30% and have a reflection coefficient of at least 50%. In one embodiment, the ultraviolet reflective layer can include a diffusive ultraviolet reflective layer. The diffusive ultraviolet reflective layer can include a coating or thin film of a fluoropolymer. The examples of fluoropolymers described herein are suitable as an ultraviolet reflective material that can enable diffusive reflectivity within the cavity 720 of the housing 710.

The ultraviolet medical device illuminator 700 can further include a fastener mechanism to aid in securely fastening the medical probe instrument 705 within the cavity 720 of the housing 710. In one embodiment, the fastener mechanism can include a magnetic coupling member 725 having a material (e.g., iron) that can magnetically attach by attraction to a metal strip 730 placed on an outer surface of the medical probe instrument 705. In one embodiment, the magnetic coupling member 725 and the metal strip 730 can form a step when each are coupled to each other. The fastener mechanism formed from the magnetic coupling member 725 and the metal strip 730 are not meant to limit the types of fasteners that can be used with the ultraviolet medical device illuminator 700. Other fastener mechanisms can include, but are not limited to, clips, tabs, hook and loop fasteners, mechanical fasteners (e.g., threaded connections), friction type fastening devices placed between two surfaces, etc.

The ultraviolet radiation sources 124, the sensors 130 and the control unit 128 can be integrated within the housing 710. In one embodiment, the ultraviolet radiation sources 124 and the sensors 130 can insert in the cavity 720, while the ultraviolet cleaning treatment 128 can also be located in the cavity, or in another layer of the housing 710, or on the exterior of the housing. In operation, the ultraviolet radiation sources 124 can be configured to emit the ultraviolet radiation to any surface that has contact with patients, while the sensors 130 can be configured to obtain various measurements such as those mentioned above during a cleaning treatment operation. All of the sensors described herein are suitable for use with this embodiment. The types of sensors 130 that are used can vary on many factors including, but not limited to, the type of cleaning desired, the type of medical probe instrument that is being cleaned, the size, etc. The control unit 128 can process the measurements obtained from the sensors 130 to control the cleaning treatment operation. It is understood, the control unit 128 could have the same components as described elsewhere herein and operate to perform those noted functions in a like manner to effectuate a cleaning treatment on the medical probe instrument 705.

Furthermore, it is understood that there are multiple possible configurations for implementing the ultraviolet radiation sources 124, the sensors 130 and the control unit 128 within the ultraviolet medical device illuminator 700. The amount and location of the ultraviolet radiation sources 124, the sensors 130 and the control unit 128 can vary. For example, the ultraviolet radiation sources 124 can be interspersed with the sensors 130 in a perimeter-type orientation wherein all of the contacting surfaces of the medical probe instrument 705 are within a field of view of the radiation sources and the sensors. In another embodiment, the ultraviolet radiation sources 124 and the sensors 130 can be separated such that each occupies different portions of space within the housing 710.

FIG. 8 shows a schematic of an ultraviolet cleaning treatment system 800 that can be implemented with any of the ultraviolet medical device illuminators depicted in FIGS. 1-7 according to an embodiment. In this embodiment, the ultraviolet cleaning treatment system 800 is shown including the ultraviolet radiation sources 124 (UV radiation source(s)) and the sensors 130 for the purposes of illustrating the interaction of all of the components that are used to provide a cleaning treatment to a particular medical device, instrument or equipment.

As depicted in FIG. 8 and described herein, the ultraviolet cleaning treatment system 800 can include a control unit 128. In one embodiment, the control unit 128 can be implemented as a computer system 820 including an analysis program 830, which makes the computer system 820 operable to manage the ultraviolet radiation sources 124 and the sensors 130 in the manner described herein. In particular, the analysis program 830 can enable the computer system 820 to operate the ultraviolet radiation sources 124 to generate and direct ultraviolet radiation towards a surface of a medical device and process data corresponding to one or more attributes regarding the device, which can be acquired by the sensors 130, and/or an ultraviolet radiation history stored as medical device data 840. The computer system 820 can individually control each ultraviolet radiation source 124 and sensor 130 and/or control two or more of the ultraviolet radiation sources and the sensors as a group. Furthermore, the ultraviolet radiation sources 124 can emit ultraviolet radiation of substantially the same wavelength or of multiple distinct wavelengths.

In an embodiment, during an initial period of operation (e.g., while the medical device is placed in a housing, receptacle, container and/or the like), the computer system 820 can acquire data from at least one of the sensors 130 regarding one or more attributes of the device and generate data 840 for further processing. The data 840 can include information regarding a presence of biological activity (e.g., microorganisms, viruses, bacteria, and/or the like) on a surface of the medical device, a frequency of usage of the medical device, a disinfection schedule history for the device, an amount of radiation (e.g., ultraviolet, infrared, visible, and/or microwave) detected, and/or the like. The computer system 820 can use the data 840 to control one or more aspects of the ultraviolet radiation generated by the ultraviolet radiation source(s) 124 during a cleaning treatment.

Furthermore, one or more aspects of the operation of the ultraviolet radiation sources 124 can be controlled or adjusted by a user 812 via an external interface I/O component 826B. The external interface I/O component 826B can be located on the exterior of any of the aforementioned medical device illuminators, and used to allow the user 812 to selectively turn on/off the ultraviolet radiation sources 124. However, it is understood that, in order to turn on the ultraviolet radiation sources 124, the computer system 820 can first determine that a device has been securely placed within a housing, receptacle, container, or the like (e.g., via data acquired by one or more sensors 130).

The external interface I/O component 826B can include, for example, a touch screen that can selectively display user interface controls, such as control dials, which can enable the user 812 to adjust one or more of: an intensity, scheduling, and/or other operational properties of the set of ultraviolet radiation sources 124 (e.g., operating parameters, radiation characteristics). In an embodiment, the external interface I/O component 826B could conceivably include a keyboard, a plurality of buttons, a joystick-like control mechanism, and/or the like, which can enable the user 812 to control one or more aspects of the operation of the set of ultraviolet radiation sources 824. The external interface I/O component 826B also can include any combination of various output devices (e.g., an LED, a visual display), which can be operated by the computer system 820 to provide status information pertaining to a cleaning treatment of a medical device for use by the user 812. For example, the external interface I/O component 826B can include one or more LEDs for emitting a visual light for the user 812, e.g., to indicate a status of the cleaning treatment. In an embodiment, the external interface I/O component 826B can include an speaker for providing an alarm (e.g., an auditory signal), e.g., for signaling that ultraviolet radiation is being generated or that a cleaning treatment has finished.

The computer system 820 is shown including a processing component 822 (e.g., one or more processors), a storage component 824 (e.g., a storage hierarchy), an input/output (I/O) component 826A (e.g., one or more I/O interfaces and/or devices), and a communications pathway 828. In general, the processing component 822 executes program code, such as the analysis program 830, which is at least partially fixed in the storage component 824. While executing program code, the processing component 822 can process data, which can result in reading and/or writing transformed data from/to the storage component 824 and/or the I/O component 826A for further processing. The pathway 828 provides a communications link between each of the components in the computer system 820. The I/O component 826A and/or the external interface I/O component 826B can comprise one or more human I/O devices, which enable a human user 812 to interact with the computer system 820 and/or one or more communications devices to enable a system user 812 to communicate with the computer system 820 using any type of communications link. To this extent, during execution by the computer system 820, the analysis program 830 can manage a set of interfaces (e.g., graphical user interface(s), application program interface, and/or the like) that enable human and/or system users 812 to interact with the analysis program 830. Furthermore, the analysis program 830 can manage (e.g., store, retrieve, create, manipulate, organize, present, etc.) the data, such as data 840, using any solution.

In any event, the computer system 820 can comprise one or more general purpose computing articles of manufacture (e.g., computing devices) capable of executing program code, such as the analysis program 830, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 830 can be embodied as any combination of system software and/or application software.

Furthermore, the analysis program 830 can be implemented using a set of modules 832. In this case, a module 832 can enable the computer system 820 to perform a set of tasks used by the analysis program 830, and can be separately developed and/or implemented apart from other portions of the analysis program 830. When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent monitoring and/or control systems that may perform a process described herein with regard to the control unit, the ultraviolet radiation sources and the sensors. To this extent, in other embodiments, the functionality provided by the computer system 820 and the analysis program 830 can be at least partially be implemented by one or more computing devices that include any combination of general and/or specific purpose hardware with or without program code. In each embodiment, the hardware and program code, if included, can be created using standard engineering and programming techniques, respectively. In another embodiment, the control unit can be implemented without any computing device, e.g., using a closed loop circuit implementing a feedback control loop in which the outputs of one or more sensors are used as inputs to control the operation of the cleaning treatment. Illustrative aspects of the invention are further described in conjunction with the computer system 820. However, it is understood that the functionality described in conjunction therewith can be implemented by any type of monitoring and/or control system.

Regardless, when the computer system 820 includes multiple computing devices, the computing devices can communicate over any type of communications link. Furthermore, while performing a process described herein, the computer system 820 can communicate with one or more other computer systems, such as the user 812, using any type of communications link. In either case, the communications link can comprise any combination of various types of wired and/or wireless links; comprise any combination of one or more types of networks; and/or utilize any combination of various types of transmission techniques and protocols.

All of the components depicted in FIG. 8 can receive power from a power component 845. The power component 845 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power component can include solar, a mechanical energy to electrical energy converter such as a piezoelectric crystal, a rechargeable device, etc.

FIG. 9 shows a schematic of an illustrative environment 900 in which the control unit 128 depicted in FIG. 8 can be used to facilitate a cleaning treatment of a medical device according to an embodiment. In this embodiment, the computer system 820 of the control unit 128 can be configured to control the ultraviolet radiation sources 124 to direct ultraviolet radiation at a surface of the medical device 102 as described herein. The sensors 130 are configured to acquire data processed by the computer system 820 to monitor a set of attributes regarding the cleaning treatment of the medical device 102 over a period of time. As illustrated, the sensors 130 can acquire data used by the computer system 820 to monitor the set of attributes (e.g., operating parameters, ultraviolet radiation characteristics).

It is understood that the set of attributes for the medical device 102 can include any combination of one or more of: a frequency of the usage of the device 102, a presence of biological activity on a surface of the device 102, a usage of the device 102, a disinfection schedule history for the device 102, and/or the like.

In the case of determining a presence of biological activity on the medical device 102, a sensor 130 can also determine a location of the biological activity, a type of biological activity (e.g., type of organism), a concentration of the biological activity, an estimated amount of time an organism has been in a growth phase (e.g., exponential growth and/or stationary), and/or the like. Furthermore, a sensor 130 can determine information on the variation of the biological activity over time, such as a growth rate, a rate with which an area including the biological activity is spreading, and/or the like. In an embodiment, a set of biological activity dynamics are related to various attributes of bacteria and/or virus activity present on a surface of the medical device 102, including, for example, the presence of detectable bacteria and/or virus activity, measured bacteria and/or virus population/concentration time dynamics, growth phase, and/or the like.

The computer system 820 can be configured to control and adjust a direction, an intensity, a pattern, and/or a spectral power (e.g., wavelength) of the set of ultraviolet radiation sources 124, based on data received from the sensors 130. The computer system 820 can control and adjust each property of the set of ultraviolet radiation sources 124 independently. For example, the computer system 820 can adjust the intensity, time duration, and/or time scheduling (e.g., including duration (e.g., exposure/illumination time)), duty cycle, time between exposures/illuminations, and/or the like) of the ultraviolet radiation source 124 for a given wavelength. Each of the properties of the ultraviolet radiation sources 124 can be adjustable and controlled by the computer system 820 according to data provided by the sensors 130.

For example, the computer system 820 can be configured to adjust the direction of the ultraviolet radiation according to a location of the biological activity detected on a surface of the medical device 102 using any solution. The computer system 820 can be configured to utilize a target timing, intensity, and/or spectral power of the ultraviolet radiation according to a type of biological activity. That is, the sensors 130 can sense locations of higher levels of biological activity on the surface of the medical device 102, and the ultraviolet radiation sources 124 can be configured by the computer system 820 to direct higher doses (by increasing intensity or exposure) of ultraviolet radiation at the locations with higher levels of biological activity (e.g., non-uniform ultraviolet radiation).

In one embodiment, the computer system 820 can be configured to set a periodic or an aperiodic schedule for the ultraviolet radiation when the medical device 102 is in place within a housing, receptacle, container or the like that is associated with any of the aforementioned ultraviolet medical device illuminators. This (periodic or aperiodic) schedule can be interrupted when a sensor senses that a surface of the medical device 102 is removed from the illuminators. In this manner, the computer system 820 can be configured to turn off the ultraviolet radiation.

As noted above, one of the sensors 130 can include a radiation detector for detecting an amount of radiation to which a surface is exposed during a cleaning treatment. The radiation can include any type of radiation, including, for example, ultraviolet, visible, infrared, microwave, and/or the like. The amount of radiation to which the surface is exposed can be used by the computer system 820 to determine if any additional radiation is required for disinfection.

It is understood that the environment 900 may include the power component 845 to supply power to one or more of the various components depicted in FIG. 9, such as the ultraviolet radiation sources 124, the sensors 130, the computer system 820, and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system, comprising:
   an open-ended housing having a cavity formed therein that is configured to receive a medical device;
   at least one ultraviolet radiation source located within the cavity of the housing that is configured to emit ultraviolet radiation towards a surface of the medical device located within the cavity;
   at least one sensor located within the cavity of the housing that is configured to generate a set of signals corresponding to at least one cavity parameter;
   a control unit that determines whether the medical device needs a cleaning treatment in response to the medical device being placed within the housing, the control unit determining that the medical device needs the cleaning treatment in response to determining, using at least one of the set of signals received from the at least one sensor, that the surface of the medical device has an amount of at least one of: bacteria, germs, or viruses, that exceeds a predetermined threshold, the control unit activating operation of the ultraviolet radiation source in response to determining that the medical device needs the cleaning treatment, wherein the activating includes specifying a plurality of operating parameters for the cleaning treatment of the medical device, the plurality of operating parameters including a cleaning treatment time that the ultraviolet radiation source emits the ultraviolet radiation towards the surface of the medical device, a dosage of ultraviolet radiation delivered by the ultraviolet radiation source, a power setting for operating the ultraviolet radiation source, and a maximum operating temperature;
   an input component that permits a user to adjust at least one of the plurality of operating parameters; and
   an output component that provides status information of the cleaning treatment for use by the user.

2. The system of claim 1, wherein the medical device comprises a stethoscope having a chest piece with a diaphragm and a bell that is configured to attach securely within the cavity of the housing for a cleaning treatment.

3. The system of claim 1, wherein the medical device is a medical probe instrument.

4. The system of claim 1, wherein the control unit is configured to interrupt operation of the ultraviolet radiation source in response to determining that the temperature of the cleaning treatment has exceeded the maximum operating temperature, and wherein the control unit is further configured to resume the cleaning treatment after a predetermined cooling time has lapsed.

5. The system of claim 1, wherein a portion of the cavity of the housing has an ultraviolet reflective layer.

6. The system of claim 5, wherein the ultraviolet reflective layer comprises a fluoropolymer.

7. The system of claim 1, wherein the housing is a flexible receptacle having an opening to an inner surface that is reflective to at least 30% that receives the medical device, and an overlapping opening cover that covers the opening in response to the medical instrument being inserted therein, and prevents ultraviolet radiation from escaping the receptacle during a cleaning treatment of the medical device.

8. The system of claim 1, wherein the open-ended housing comprises one side that is open.

9. The system of claim 8, wherein the open side of the open-ended housing is configured to attach to the medical device upon placement therewith.

10. The system of claim 9, wherein the surface of the medical device faces the at least one ultraviolet radiation source within the cavity of the open-ended housing, wherein the surface of the medical device is a patient contact surface.

11. The system of claim 8, wherein the open side of the open-ended housing comprises an outer rim that extends beyond the cavity, the outer rim configured to accommodate the medical device upon placement against the open side, the medical device sitting in the outer rim upon placement against the open side with the surface of the medical device in substantial alignment with an opening into the cavity.

12. The system of claim 1, wherein the at least one sensor includes at least one operating parameter sensor configured to monitor one of the plurality of operating parameters during the cleaning treatment and provide signals thereof to the control unit, wherein the control unit controls operation of the cleaning treatment as a function of the signals received from the at least one operating parameter sensor.

13. The system of claim 12, wherein the at least one operating parameter sensor is interspersed with the at least one ultraviolet radiation source.

14. The system of claim 1, wherein the at least one sensor comprises a bacterial fluorescence sensor configured to detect the amount of the at least one of: bacteria, germs, or viruses, that is present on the surface of the medical device.

15. The system of claim 14, wherein the bacterial fluorescence sensor generates signals representative of a condition of the surface of the medical device with respect to the amount of the at least one of: bacteria, germs, or viruses, and sends the signals to the control unit, the control unit determining whether the cleaning treatment is necessary as a function of the signals provided by the bacterial fluorescence sensor.

16. The system of claim 12, wherein the at least one operating parameter sensor comprises a temperature sensor configured to detect the temperature of the cavity and the surface of the medical device during the cleaning treatment while the at least one ultraviolet radiation is in operation, the temperature sensor generating signals representative of the detected temperature and sending the signals to the control unit.

17. The system of claim 1, wherein the at least one ultraviolet radiation source comprises a plurality of ultraviolet radiation sources configured to function in a coordinated manner.

18. The system of claim 17, wherein each of the plurality of ultraviolet radiation sources operate at the same wavelength and intensity for the same duration.

19. The system of claim 17, wherein the plurality of ultraviolet radiation sources comprises a first set of ultraviolet radiation sources configured to operate at a target wavelength and intensity that is designed for the disinfection of one type of bacteria and/or viruses, and a second set of ultraviolet radiation sources configured to operate at a different target wavelength and intensity that is designed for disinfection of a different type of bacteria and/or viruses.

20. The system of claim 5, wherein the ultraviolet reflective layer comprises a diffusive ultraviolet reflective layer.

* * * * *